(12) United States Patent
Jucker et al.

(10) Patent No.: US 8,691,763 B2
(45) Date of Patent: Apr. 8, 2014

(54) METHODS FOR TREATING OR PREVENTING CARDIOVASCULAR DISORDERS AND PROVIDING CARDIOVASCULAR PROTECTION

(75) Inventors: Beat M. Jucker, King of Prussia, PA (US); John J. Lepore, King of Prussia, PA (US); Eric J. Olson, King of Prussia, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

(21) Appl. No.: 13/695,976

(22) PCT Filed: May 4, 2011

(86) PCT No.: PCT/US2011/035114
§ 371 (c)(1),
(2), (4) Date: Nov. 2, 2012

(87) PCT Pub. No.: WO2011/140176
PCT Pub. Date: Nov. 10, 2011

(65) Prior Publication Data
US 2013/0053317 A1   Feb. 28, 2013

Related U.S. Application Data

(60) Provisional application No. 61/331,010, filed on May 4, 2010, provisional application No. 61/350,144, filed on Jun. 1, 2010, provisional application No. 61/422,701, filed on Dec. 14, 2010.

(51) Int. Cl.
| | | |
|---|---|---|
| *A61K 38/26* | (2006.01) | |
| *A61P 3/10* | (2006.01) | |
| *A61P 7/12* | (2006.01) | |
| *C07K 14/605* | (2006.01) | |
| *A61K 38/38* | (2006.01) | |
| *A61K 47/48* | (2006.01) | |
| *C07K 14/76* | (2006.01) | |
| *A61K 38/00* | (2006.01) | |
| *A61P 9/00* | (2006.01) | |

(52) U.S. Cl.
USPC .................. 514/11.7; 514/15.2; 514/16.4

(58) Field of Classification Search
None
See application file for complete search history.

(56) References Cited

U.S. PATENT DOCUMENTS

| | | | |
|---|---|---|---|
| 5,512,549 A | 4/1996 | Chen et al. | |
| 5,545,618 A | 8/1996 | Buckley et al. | |
| 6,277,819 B1 | 8/2001 | Efendic | |
| 6,284,725 B1 | 9/2001 | Coolidge et al. | |
| 6,329,336 B1 | 12/2001 | Bridon et al. | |
| 6,380,357 B2 | 4/2002 | Hermeling et al. | |
| 6,706,689 B2 | 3/2004 | Coolidge et al. | |
| 6,747,006 B2 | 6/2004 | Efendic | |
| 6,875,432 B2 | 4/2005 | Liu et al. | |
| 6,894,024 B2 | 5/2005 | Coolidge et al. | |
| 7,141,547 B2 | 11/2006 | Rosen et al. | |
| 7,189,690 B2 | 3/2007 | Rosen et al. | |
| 7,238,660 B2 | 7/2007 | Rosen et al. | |
| 7,238,667 B2 | 7/2007 | Rosen et al. | |
| 7,259,233 B2 | 8/2007 | Dodd et al. | |
| 7,271,149 B2 | 9/2007 | Glaesner et al. | |
| 7,521,423 B2 | 4/2009 | Young et al. | |
| 7,521,424 B2 | 4/2009 | Rosen et al. | |
| 7,569,384 B2 | 8/2009 | Rosen et al. | |
| 7,671,023 B2 | 3/2010 | Laugero et al. | |
| 7,790,681 B2 | 9/2010 | Hathaway et al. | |
| 7,888,314 B2 | 2/2011 | Hathaway et al. | |
| 7,977,306 B2 * | 7/2011 | Rosen et al. .................. | 514/7.2 |
| 8,071,539 B2 * | 12/2011 | Rosen et al. .................. | 514/7.2 |
| 2003/0220255 A1 | 11/2003 | Knudsen et al. | |
| 2005/0054570 A1 | 3/2005 | Rosen et al. | |
| 2007/0111940 A1 | 5/2007 | Larsen et al. | |
| 2007/0128193 A1 | 6/2007 | O'Neil et al. | |
| 2008/0194672 A1 * | 8/2008 | Hoveyda et al. .............. | 514/450 |
| 2008/0200383 A1 | 8/2008 | Jennings et al. | |
| 2008/0254087 A1 | 10/2008 | Bush et al. | |
| 2008/0300173 A1 | 12/2008 | DeFrees | |
| 2009/0215688 A1 | 8/2009 | Knudsen et al. | |
| 2009/0325873 A1 | 12/2009 | O'Neil et al. | |
| 2010/0009910 A1 | 1/2010 | Bush et al. | |
| 2010/0029554 A1 | 2/2010 | Ghosh et al. | |
| 2010/0311662 A1 | 12/2010 | Coolidge et al. | |
| 2011/0301080 A1 | 12/2011 | Bush et al. | |

FOREIGN PATENT DOCUMENTS

| | | |
|---|---|---|
| EP | 0964692 B1 | 12/1999 |
| EP | 1330261 B1 | 7/2003 |
| WO | WO 98/08531 A1 | 3/1998 |

(Continued)

OTHER PUBLICATIONS

Kadish et al "Device Therpaies in the Post-Myocardial Infarction Patient with Left Ventricular Dysfunction" Am J Cardiol 102:29G-37G. Published 2008.*
Scott RL "Angiotensin-Converting Enzyme Inhibitor and/or Angiotensin Receptor Antagonists for the Postmyocardial Infarction Patient" Cardiol Clin 26:73-77. Published Feb. 2008.*
Taggart D "Coronary artery bypass graft vs. percutaneous angioplasty: CABG on the rebound?" Curr Opin Cardiol 22:517-523. Published 2007.*
Nordqvist C "What Is a Heart Attack? What Causes a Heart Attack?" Medical News Today. Accessed on the Internet Jan. 24, 2013. Published May 27, 2009.*
Bao et al "Albiglutide, a Long Lasting Glucagon-Like Peptide-1 Analog, Protects the Rat Heart against Ischemia/Reperfusion Injury: Evidence for Improving Cardiac Metabolic Efficiency" PLoS ONE 6:1-10. Published Aug. 26, 2011.*

(Continued)

*Primary Examiner* — Cecilia J Tsang
*Assistant Examiner* — Zachary J Miknis
(74) *Attorney, Agent, or Firm* — Andrea V. Lockenour; William T Han; Carl W. Battle

(57) ABSTRACT

The present invention provides methods for treating, preventing and/or ameliorating at least one cardiovascular disorder in a human in need thereof comprising administering to said human a pharmaceutical composition comprising at least one polypeptide having at least one GLP-1 activity and/or at least one GLP-1 agonist.

4 Claims, 19 Drawing Sheets

(56) References Cited

FOREIGN PATENT DOCUMENTS

| WO | WO 03/040309 A1 | 10/2002 |
|---|---|---|
| WO | WO 03/033671 A2 | 4/2003 |
| WO | WO 03/058203 A2 | 7/2003 |
| WO | WO 03/084563 A1 | 10/2003 |
| WO | WO 2004/056313 A2 | 7/2004 |
| WO | WO 2004/056317 A2 | 7/2004 |
| WO | WO 2005/120492 | 12/2005 |
| WO | WO 2006/073890 A2 | 7/2006 |
| WO | WO 2006/110887 A2 | 10/2006 |
| WO | WO 2007/056681 A2 | 5/2007 |
| WO | WO 2007/140284 A2 | 12/2007 |
| WO | WO 2008/019143 A2 | 2/2008 |

OTHER PUBLICATIONS

Halbirk, et al., "Cardiovascular and Metabolic Effects of 48-Hour Glucagon-like Peptide 1 Infusion in Compensated Chronic Heart Failure Patients," *Am. J. Physiol. Heart Circ Physiol.* (Jan. 15, 2010).

Read, et al., "DPP-4 Inhibition by Sitagliptin Improves the Myocardial Response to Dobutamine Stress and Mitigates Stunning in a Pilot Study of Patients With Coronary Artery Disease," *Circ. Cardiovasc. Imaging*, vol. 3, pp. 195-201 (2010).

Poornima, et al., "Chronic Glucagon-Like Peptide-1 Infusion Sustains Left Ventricular Systolic Function and Prolongs Survival in the Spontaneously Hypertensive, Heart Failure-Prone Rat", Circ. Heart Fail., vol. 1, pp. 153-160 (2008).

Grieve, et al., Emerging cardiovascular actions of the incretin hormone glucagon-like peptide-1: potential therapeutic benefits beyond glycaemic control?,*British Journal of Pharmacology*, vol. 157, pp. 1340-1351 (2009).

Fields, et al., "Glucagon-like Peptide-1 and Myocardial Protection: More than Glycemic Control", Clin. Cardiol. vol. 32, No. 5, pp. 236-243 (2009).

Mafong, et al., "The Role of Incretins in Cardiovascular Control", *Current Hypertension Reports*, vol. 11, pp. 18-22 (2009).

Nyström, et al., The Potential Beneficial Role of Glucagon-like Peptide-1 in Endothelial Dysfunction and Heart Failure Associated with Insulin Resistance, Horm. Metab. Res., vol. 40, pp. 593-606 (2008).

Sokos, et al., "Glucagon-like peptide-1 infusion improves left ventricular ejection fraction and functional status in patients with chronic heart failure", *J. Card. Fail.* vol. 12, No. 9, pp. 694-699 (2006).

Taegtmeyer H., "Cardiac metabolism as a target for the treatment of heart failure", *Circulation*, vol. 110, No. 8, pp. 894-896 (2004).

Nikolaidis, et al., "Effects of glucagon-like peptide-1 in patients with acute myocardial infarction and left ventricular dysfunction after successful reperfusion", *Circulation*, vol. 109, No. 8, pp. 962-965 (2004).

Nikolaidis, et al., "Recombinant glucagon-like peptide-1 increases myocardial glucose uptake and improves left ventricular performance in conscious dogs with pacing-induced dilated cardiomyopathy", *Circulation*, vol. 110, No. 8, pp. 955-961 (2004).

Bose, et al., "Glucagon like peptide-1 is protective against myocardial ischemia/reperfusion injury when given either as a preconditioning mimetic or at reperfusion in an isolated rat heart model", *Cardiovasc. Drugs Ther.*, vol. 19, No. 1, pp. 9-11 (2005).

Kristensen, et al., "Lack of cardioprotection from subcutaneously and preischemic administered liraglutide in a closed chest porcine ischemia reperfusion model", *BMC Cardiovasc Disord.*, vol. 23;9:31 (2009).

Ossum, et al., "The cardioprotective and inotropic components of the postconditioning effects of GLP-1 and GLP-1(9-36)a in an isolated rat heart", Pharmacol. Res., vol. 60, No. 5, pp. 411-417 (2009).

Noyan-Ashraf, et al., GLP-1R agonist liraglutide activates cytoprotective pathways and improves outcomes after experimental myocardial infarction in mice, *Diabetes*, vol. 58, No. 4, pp. 975-983 (2009).

Xi E, et al., "Effects and mechanism of glucagon-like peptide-1 on injury of rats cardiomyocytes induced by hypoxia-reoxygenation", *Chin. Med. J. (Engl)*, vol. 121, No. 21, pp. 2134-2138 (2008).

Huisamen, et al., "Signalling pathways activated by glucagon-like peptide-1 (7-36) amide in the rat heart and their role in protection against ischaemia", *Cardiovasc. J. Afr.*, vol. 19, No. 2, pp. 77-83 (2008).

Ban, et al.,"Cardioprotective and vasodilatory actions of glucagon-like peptide 1 receptor are mediated through both glucagon-like peptide 1 receptor-dependent and -independent pathways", *Circulation*, vol. 117, No. 18, pp. 2340-2350 (2008).

Sonne, et al., "Protective effects of GLP-1 analogues exendin-4 and GLP-1(9-36) amide against ischemia-reperfusion injury in rat heart", Regul. Pept. vol. 146, No. 1-3, pp. 243-249 (2008).

Sokos, et al., "Effect of glucagon-like peptide-1 (GLP-1) on glycemic control and left ventricular function in patients undergoing coronary artery bypass grafting," *Am. J. Cardiol.*, vol. 100, No. 5, pp. 824-829 (2007).

Bose, et al., "Myocardial ischaemia-reperfusion injury is attenuated by intact glucagon like peptide-1 (GLP-1) in the in vitro rat heart and may involve the p70s6K pathway," *Cardiovasc. Drugs Ther.*, vol. 21, No. 4, pp. 253-256 (2007).

Zhao, et al., " Direct effects of glucagon-like peptide-1 on myocardial contractility and glucose uptake in normal and postischemic isolated rat hearts", *J. Pharmacol. Exp. Ther.* vol. 317, No. 3, pp. 1106-1113 (2006).

Nikolaidis, et al., "Active metabolite of GLP-1 mediates myocardial glucose uptake and improves left ventricular performance in conscious dogs with dilated cardiomyopathy", *Am. J. Physiol. Heart Circ. Physiol.*, vol. 289, No. 6, pp. H2401-H2408 (2005).

Bose, et al., "Glucagon-like peptide 1 can directly protect the heart against ischemia/reperfusion injury", *Diabetes.* vol. 54, No. 1, pp. 146-151 (2005).

Kaviani Pour, et al., "Glucagon-like peptide-1 (7-36) amide prevents the accumulation of pyruvate and lactate in the ischemic and non-ischemic porcine myocardium", *Peptides*, vol. 24, No. 4, pp. 569-578. (2003).

Gros, et al., "Cardiac function in mice lacking the glucagon-like peptide-1 receptor", *Endocrinology*, vol. 144, No. 6, pp. 2242-2252 (2003).

Luque, et al., "Glucagon-like peptide-1 (GLP-1) and glucose metabolism in human myocytes",*J. Endocrinol.*, vol. 173, No. 3, pp. 465-473 (2002).

Petroff, et al., "Glucagon-like peptide-1 increases cAMP but fails to augment contraction in adult rat cardiac myocytes", *Circ. Res.*, vol. 89, No. 5, pp. 445-452 (2001).

Timmers, et al., "Exenatide reduces infarct size and improves cardiac function in a porcine model of ischemia and reperfusion injury", J. Am. Coll. Cardiol., vol. 53, No. 6, pp. 501-510 (2009).

Nathanson, et al., "Plasma levels of glucagon like peptide-1 associate with diastolic function in elderly men", *Diabet. Med.*, vol. 28, No. 3, pp. 301-305 (2011).

Liu, et al., "Glucagon-like peptide-1 and the exenatide analogue AC3174 improve cardiac function, cardiac remodeling, and survival in rats with chronic heart failure", *Cardiovasc. Diabetol.*, vol. 16, No. 9, p. 76 (2010).

Kim, et al., Effects of Once-Weekly Dosing of a Long-Acting Release Formulation of IDG/Exenatide on Glucose Control and Body eight in Subjects with Type 2 Diabetes, Diabetes Care in Press, published online Mar. 12, 2007.

Bowie, et al., Deciphering the Message in Protein Sequences: Tolerances to Amino Acid Substitutions. Science, 247:1306-1310, Mar. 2010.

Chai and Egan, "Incretin-Based Therpaies in Type 2 Diabetes Mellitus." J Clin Endocrinol Metab, 93(10):3703-3716, Oct. 2008.

Xiao, et al. "Bioogical Activities on Glucagon-Like Peptide-1 Analogues in Vitro and in Vivo." Biochemistry, 40:2860-2869 (2001).

* cited by examiner

Figure 1    Pharmacokinetic profile following a single s.c. dose of albiglutide, 15 mg/kg, in SD rat. Ischemia-reperfusion injury study doses were chosen based on modelling of 1, 3, and 10 mg/kg dose paradigms. "A" is time in hours and "B" is actual blood concentration (ng/mL) of albiglutide.
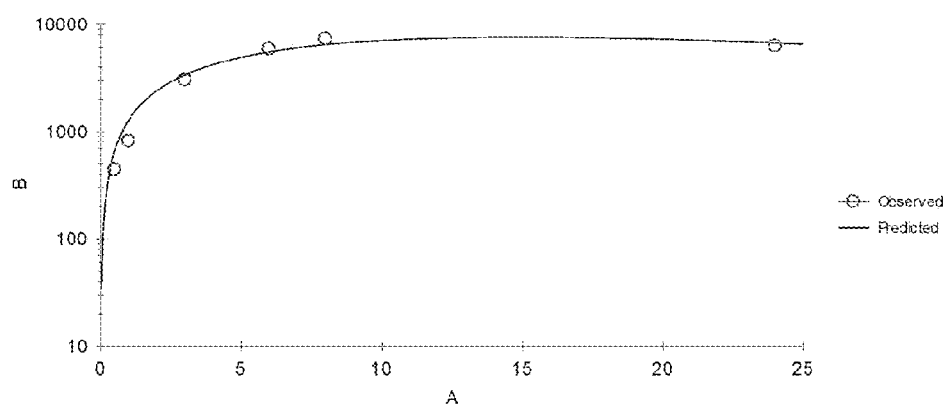

Figure 2    Myocardial ischemia-reperfusion (I/R) injury protocol. Animals were dosed at 48, 24, and 2 hrs prior to I/R injury. The left anterior descending coronary artery was occluded for 30 minutes followed by 24 hr reperfusion. Blood and heart were harvested at the end of study.

Figure 3   Transverse sections of heart depicting the area at risk and infarct staining are presented. Myocardial infarct region stained white (TTC negative), ischemic region stained red, and non-ischemic region stained dark blue. The sum of the infarct size for all 5 slices was used to determine the overall area at risk and ischemic area as a percentage of left ventricle area at risk.

Heart is cut into 5 transverse sections from base to apex for area at risk and infarct analysis

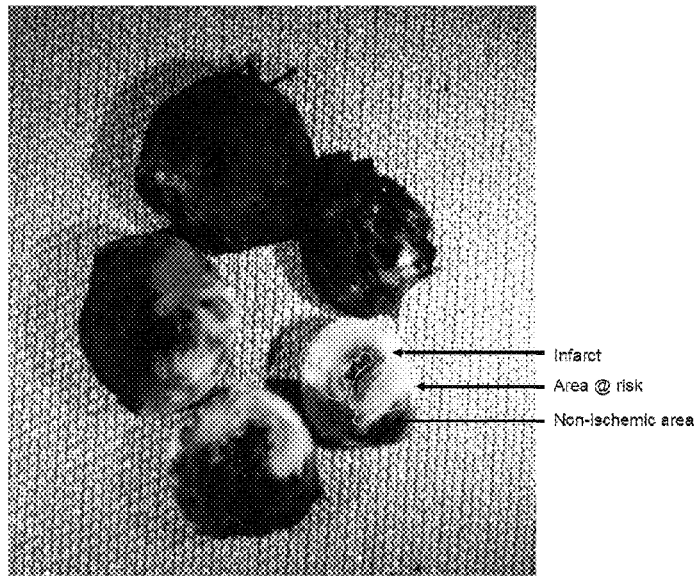

Figure 4　　The effect of albiglutide (1, 3 & 10 mg/kg) on left ventricle infarct size. Left ventricle area at risk following 30 minutes ischemia and 24 hours reperfusion was similar among the groups, indicating that animals were subjected to a similar ischemic insult. Myocardial infarct size presented as % of left ventricle area @ risk after 30 minutes ischemia and 24 hours reperfusion. Data are presented as Mean ± SEM; *p<0.05 vs. vehicle; **p<0.01 vs. vehicle.

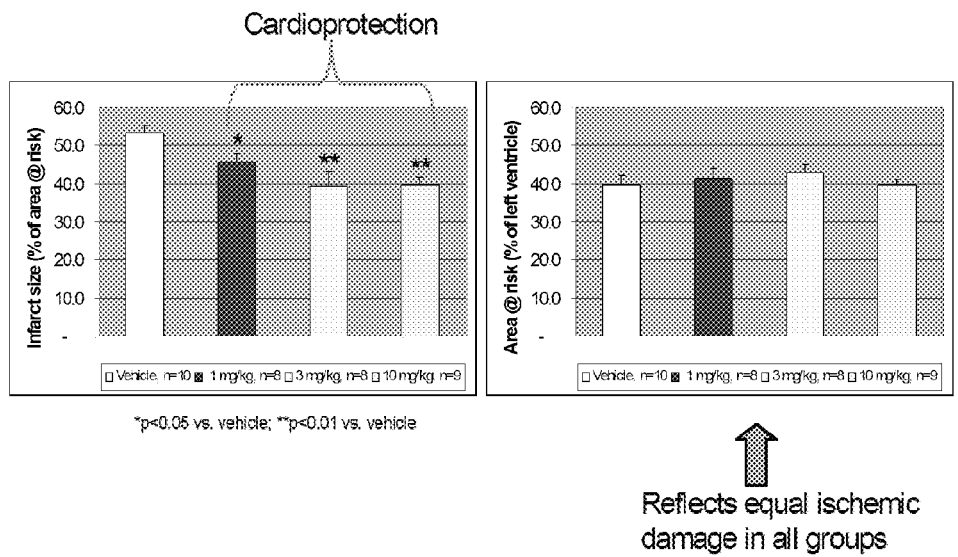

Figure 5    Recombinant human serum albumin (rHSA) was examined in the cardiac ischemia-reperfusion injury model as an additional control for albiglutide. The dose used was 2.7 mg/kg (dose equivalent to 3 mg/kg albiglutide) and administered as outlined in Figure 2. Myocardial infarct size was presented as % of left ventricle area at risk after 30 minutes ischemia and 24 hours reperfusion. Data are presented as Mean ± SEM.

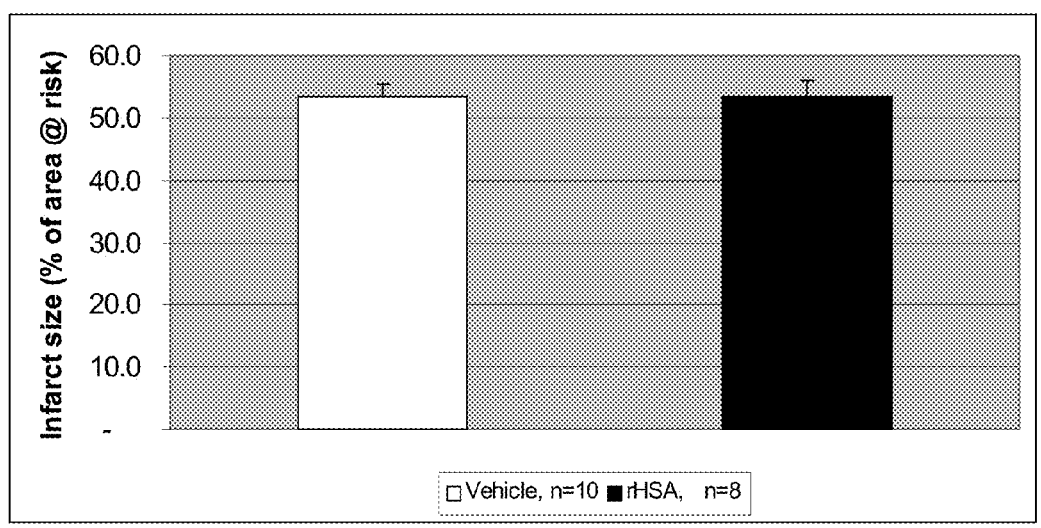

rHSA (recombinant human serum albumin, 2.7 mg/kg): dose equivalent to 3 mg/kg Albiglutide Figure 6    Body weight change and food consumption measurement over 2 days of albiglutide dosing at 1, 3, or 10 mg/kg prior to myocardial ischemia-reperfusion injury. Data are presented as Mean ± SEM; **p<0.01 vs. vehicle.
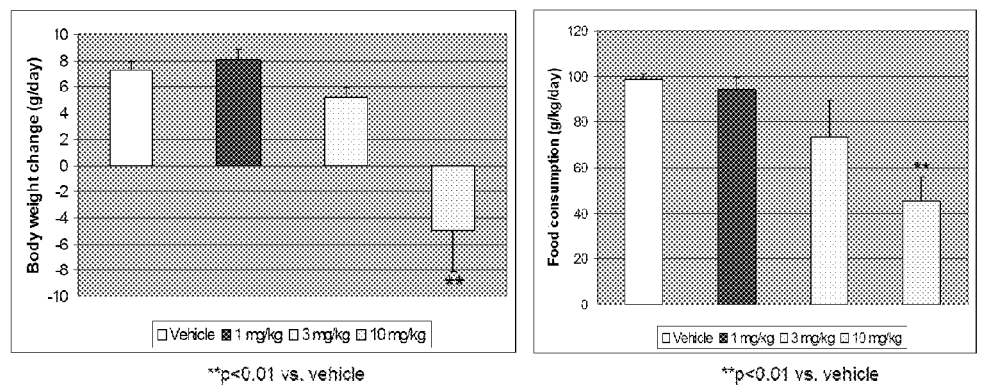

Figure 7: Cardiac function and high energy metabolites
7A
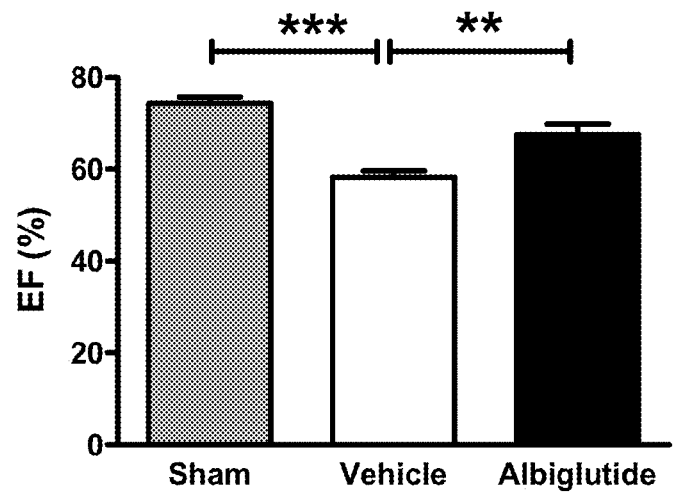
7B
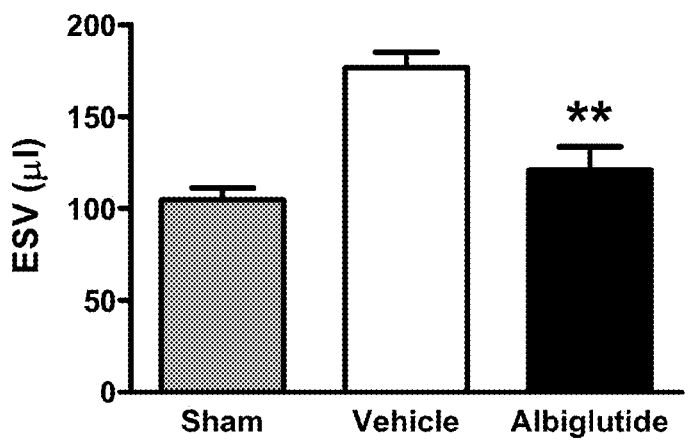

Figure 7 Continued
7C
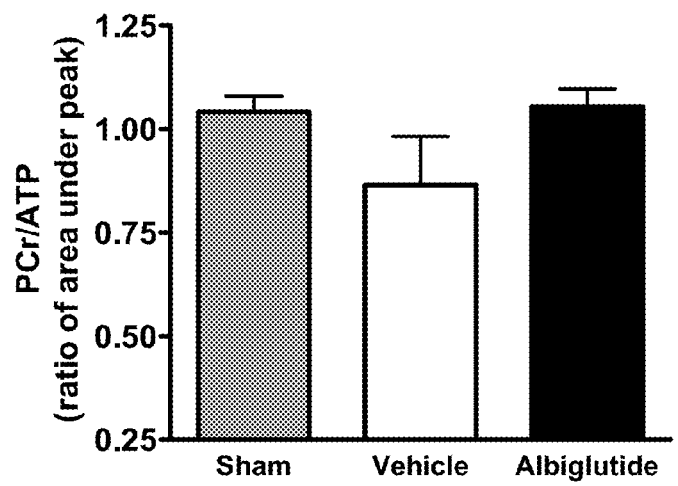
7D
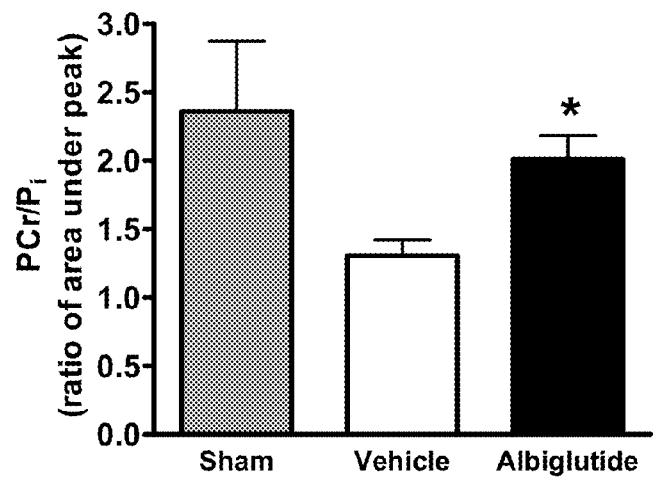

Figure 7 Continued
7E
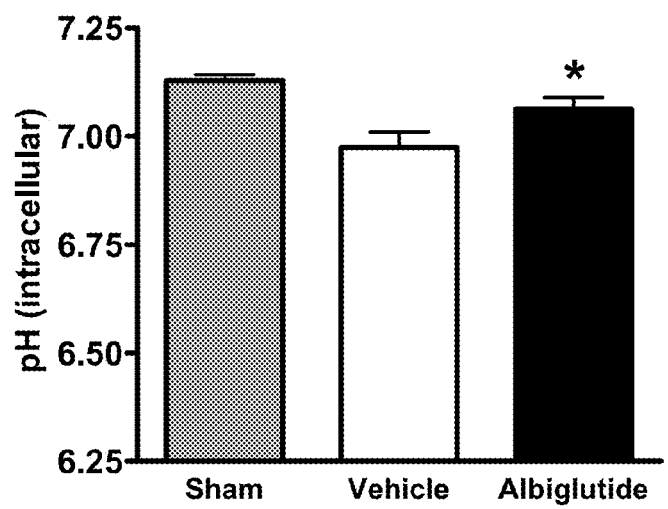
7F
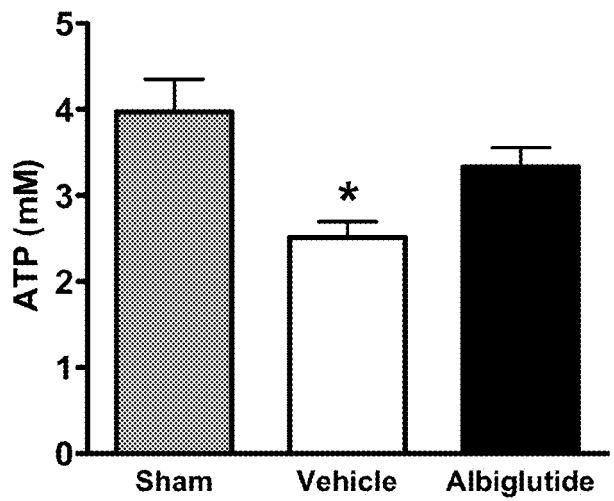

7G

Figure 8    In vivo 2-deoxyglucose experiment schematic protocol
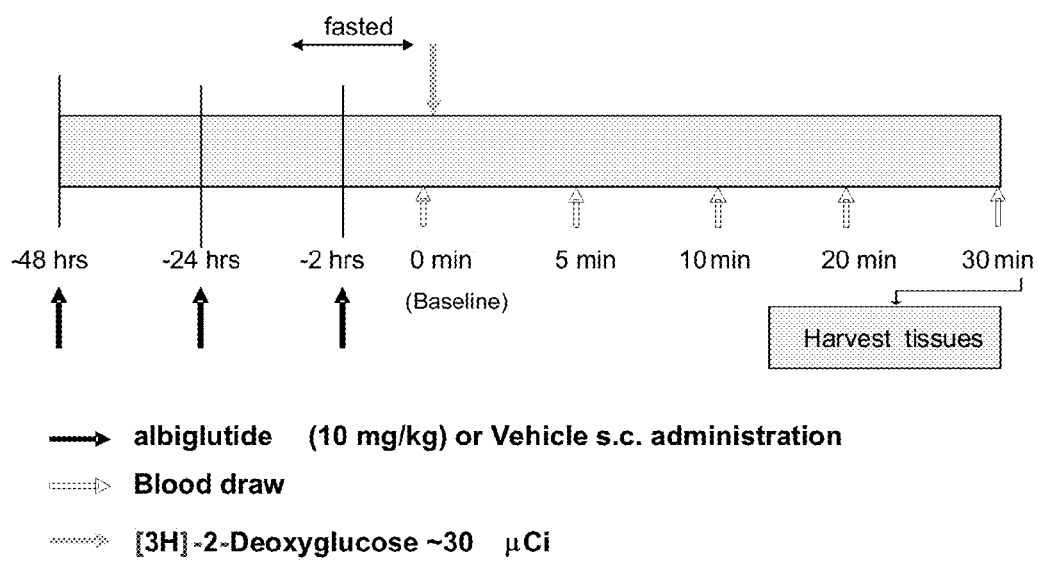

Figure 9    Daily body weight change during the experimental protocol is shown. Data are presented as mean±SEM. ***P<0.001
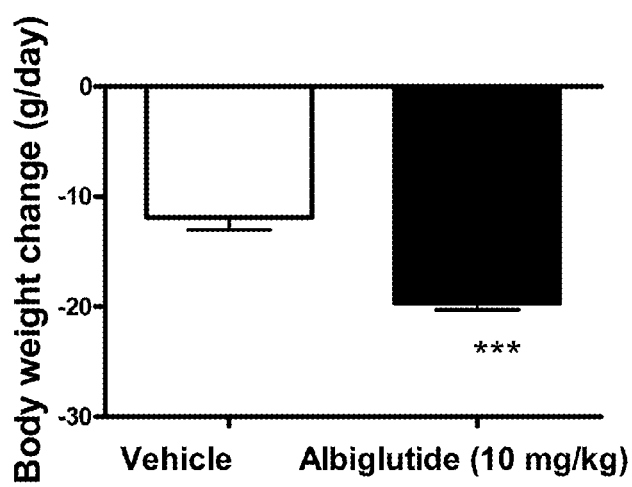

Figure 10    In vivo cardiac 2-deoxyglucose uptake in hearts of Vehicle and albiglutide treated rats. Data are presented as mean±SEM. *$P<0.03$
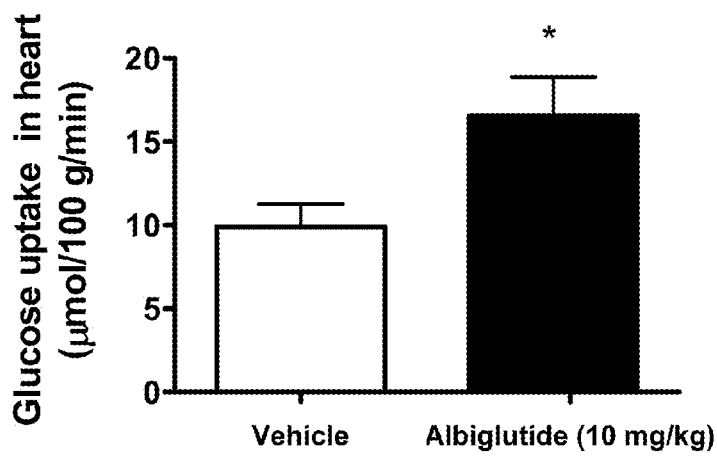

Figure 11   Ex vivo cardiac glucose metabolism experiment schematic protocol
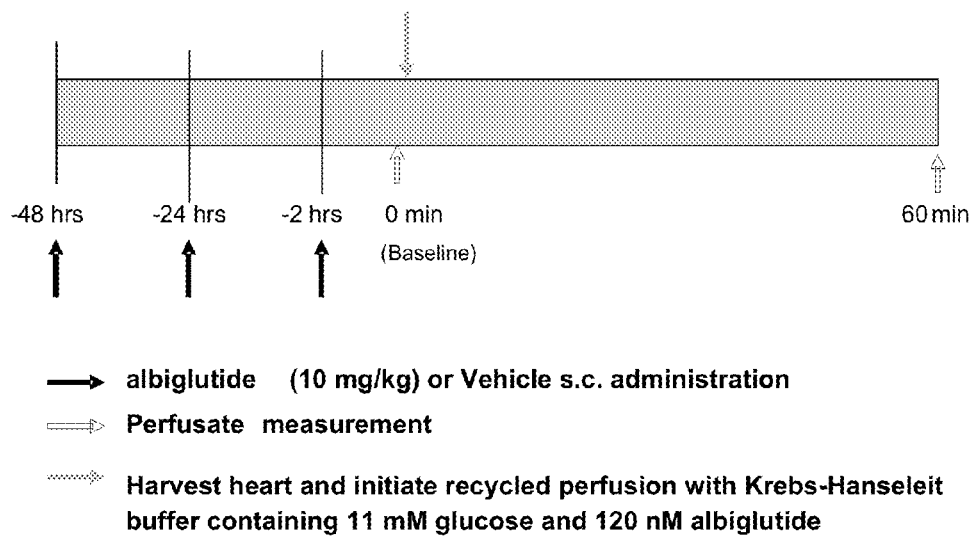

Figure 12    Schematic of the isolated perfused heart preparation (recirculation mode). Glucose and lactate were measured using an Olympus AU 640 analyzer. Glucose uptake =(Glucose$_{initial}$-Glucose$_{terminal}$) x perfusion volume/heart wet weight (g)/time (h). Lactate efflux =(Lactate$_{initial}$-Lactate$_{terminal}$) x perfusion volume/heart wet weight (g)/time (h)
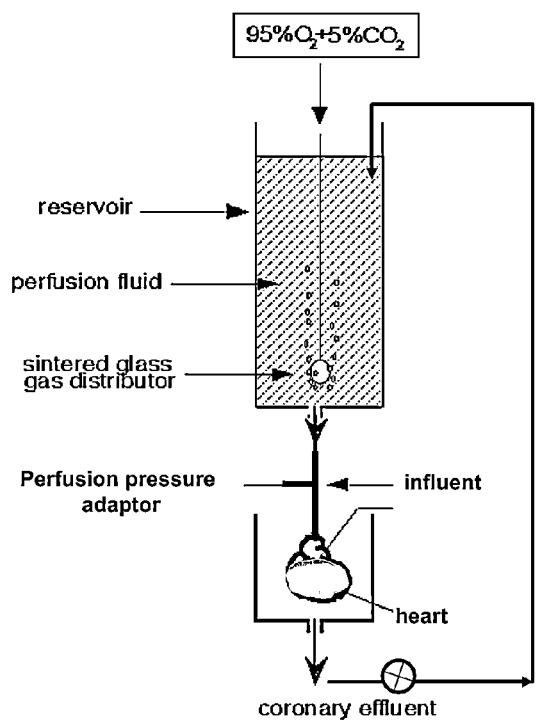

Figure 13  Glucose uptake and lactate production (efflux) by heart during a 60 min perfusion period in the Langendorff perfused heart setup. Data are presented as mean±SEM. *P<0.05
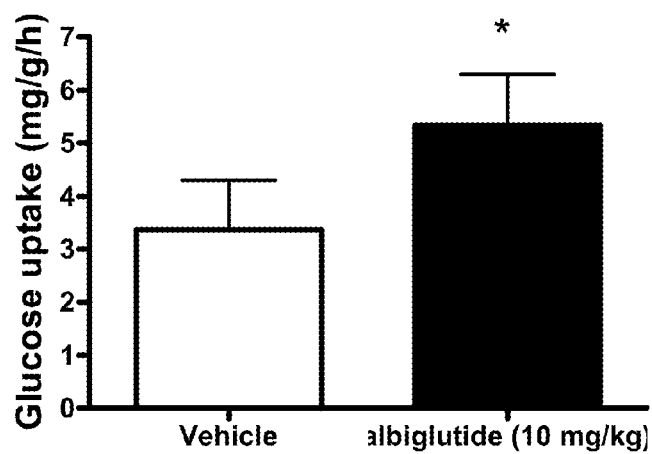
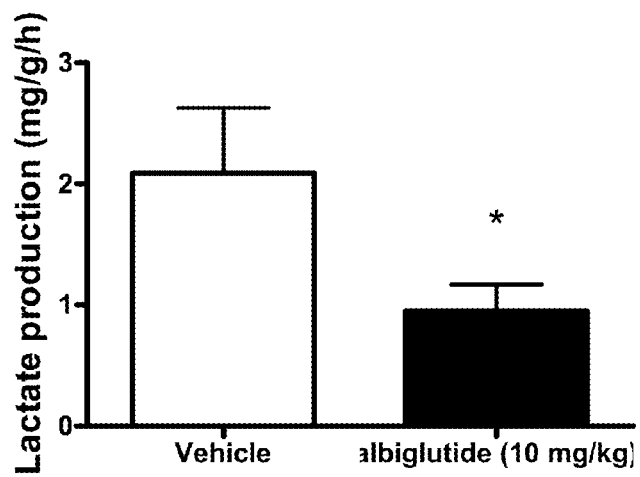

Figure 14. *In Vivo* Intermediary Glucose Metabolism in Normal Rat Hearts. Data are presented as mean±SEM *P<0.05 vs. vehicle
A
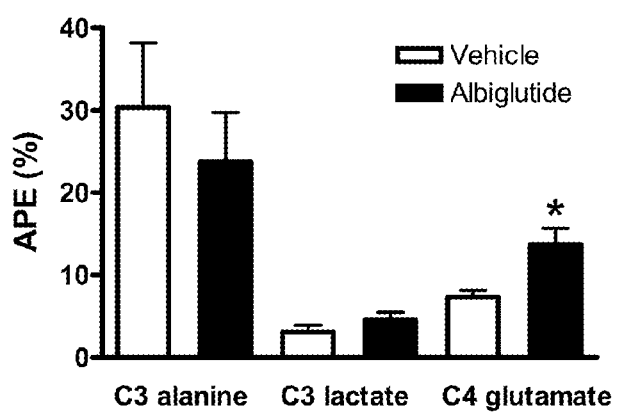
B
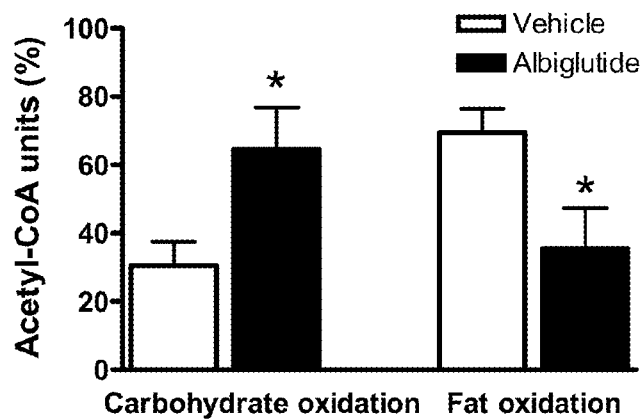

Figure 15. Lactate Disposition *Ex Vivo*. Data are presented as mean±SEM *P<0.05 vs. vehicle
A
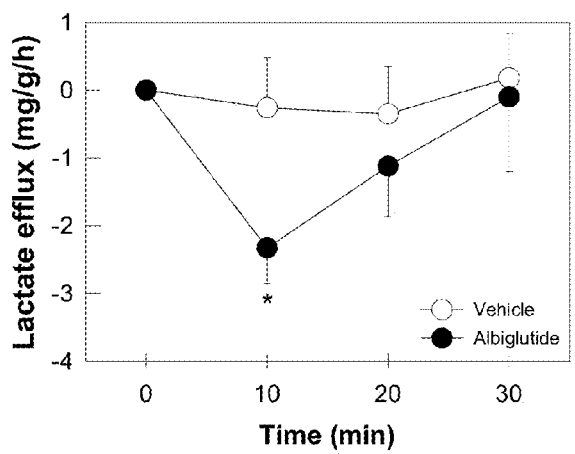
B
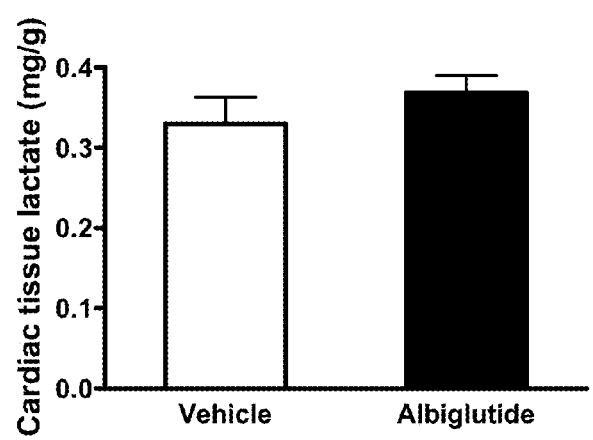
C
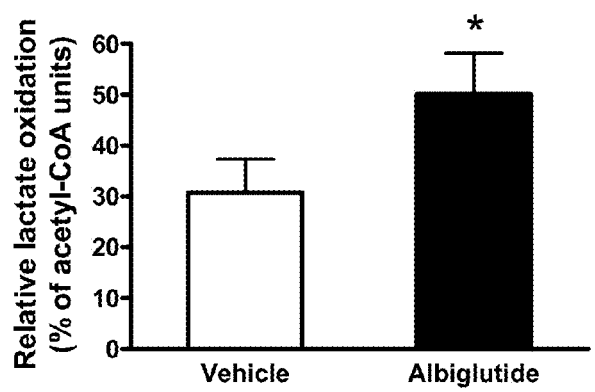

Figure 16: SEQ ID NO.: 1

SEQ ID NO.: 1

```
HGEGTFTSDVSSYLEGQAAKEFIAWLVKGRHGEGTFTSDVSSYLEGQAAKEFIAWLVKGR    60
DAHKSEVAHRFKDLGEENFKALVLIAFAQYLQQCPFEDHVKLVNEVTEFAKTCVADESAE   120
NCDKSLHTL FGDKLCTVATLRETYGEMADCCAKQEPERNECFLQHKDDNPNLPRLVRPE   180
VDVMCTAFHDNEETFLKKYLYEIARRHPYFYAPELLFFAKRYKAAFTECCQAADKAACLL   240
PKLDELRDEGKASSAKQRLKCASLQKFGERAFKAWAVARLSQRFPKAEFAEVSKLVTDLT   300
KVHTECCHGDLLECADDRADLAKYICENQDSISSKLKECCEKPLLEKSHCIAEVENDEMP   360
ADLPSLAADFVESKDVCKNYAEAKDVFLGMFLYEYARRHPDYSVVLLLRLAKTYETTLEK   420
CCAAADPHECYAKVFDEFKPLVEEPQNLIKQNCELFEQLGEYKFQNALLVRYTKKVPQVS   480
TPTLVEVSRNLGKVGSKCCKHPEAKRMPCAEDYLSVVLNQLCVLHEKTPVSDRVTKCCTE   540
SLVNRRPCFSALEVDETYVPKEFNAETFTFHADICTLSEKERQIKKQTALVELVKHKPKA   600
TKEQLKAVMDDFAAFVEKCCKADDKETCFAEEGKKLVAASQAALGL                 674
```

METHODS FOR TREATING OR PREVENTING CARDIOVASCULAR DISORDERS AND PROVIDING CARDIOVASCULAR PROTECTION

This application is a 371 of International Application No. PCT/US2011/035114, filed 4 May 2011, which is incorporated herein by reference. This application claims priority to and the benefit of U.S. Provisional Application No. 61,422, 701, filed 14 Dec. 2010, U.S. Provisional Application No. 61/350,144, filed 1 Jun. 2010 and U.S. Provisional Application No. 61/331,010, filed 4 May 2010.

This international application claims priority to U.S. Provisional Serial Application Nos. 61/331,010, filed on 4 May 2010, 61/350,144, filed on 1 Jun. 2010, and 61/422,701 filed on 14 Dec. 2010, all of which are incorporated by reference herein in their entirety.

FIELD OF THE INVENTION

The present invention relates to methods and pharmaceutical compositions for treating or preventing cardiovascular disorders and/or providing cardiovascular protection using compounds having GLP-1 activity and/or GLP-1 agonists.

BACKGROUND

Hypoglycemic agents may be used in the treatment of both type I and type II diabetes to lower glucose concentration in blood. Insulinotropic peptides have been implicated as possible therapeutic agents for the treatment of diabetes. Insulinotropic peptides include, but are not limited to, incretin hormones, for example, gastric inhibitory peptide (GIP) and glucagon like peptide-1 (GLP-1), as well as fragments, variants, and/or conjugates thereof. Insulinotropic peptides also include, for example, exendin 3 and exendin 4. GLP-1 is a naturally occurring 36 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of β-cells. In non-clinical experiments GLP-1 promotes continued beta cell competence by stimulating transcription of genes important for glucose dependent insulin secretion and by promoting beta-cell neogenesis (Meier, et al. *Biodrugs*. 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption.

Although the major physiological function of GLP-1 is associated with glycemic control, increasing evidence indicates that GLP-1 may also play an important role in cardiovascular physiology. GLP-1 receptors are also expressed in cardiovascular tissues and activation of GLP-1 receptors by agonists results in a wide range of cardiovascular effects (Grieve, et al., *British Journal of Pharmacology*. 2009; 157 (8):1340). It has been recently demonstrated that GLP-1 protects the heart against myocardial ischemia-reperfusion injury both ex vivo (Ban, et al., *Circulation*. 2008; 117:2340) and in vivo (Bose, et al., *Diabetes*. 2005; 54:146.). More importantly, it has been reported that short-term infusion of GLP-1 for 72 hours significantly improves cardiac function in patients with acute myocardial infarction (AMI), suggesting GLP-1 and mimetics may be used as a novel therapeutic approach for heart failure (Sokos, et al., *J Card Fail*. 12:694 (2006)).

Native GLP-1 has a very short serum half-life (<5 minutes). Accordingly, it is not currently feasible to exogenously administer native GLP-1 as a therapeutic treatment for diabetes. Commercially available incretin mimetics such as exenatide (Byetta®) improve glycemic control by reducing fasting and postprandial glucose concentrations when administered subcutaneously (5 μg or 10 μg BID) to patients with T2DM.

Albiglutide is a novel analogue of GLP-1 synthesized through genetic fusion of a DPP-IV resistant form of the peptide as a dimer to human albumin, which provides a long-lasting GLP-1 activity with a half-life of about 5 to 7 days.

Thus, there is a need for long lasting incretin mimetics and GLP-1 agonists that can provide treatment for and/or provide cardiovascular protection from myocardial ischemia or other cardiovascular disorders.

BRIEF DESCRIPTION OF THE DRAWINGS

FIG. 1. Pharmacokinetic profile following a single s.c. dose of albiglutide, 15 mg/kg, in SD rat. Ischemia-reperfusion injury study doses were chosen based on modeling of 1, 3, and 10 mg/kg dose paradigms.

FIG. 2: Myocardial ischemia-reperfusion (I/R) injury protocol. Animals were dosed at 48, 24, and 2 hours prior to I/R injury. The left anterior descending coronary artery was occluded for 30 minutes followed by 24 hr reperfusion. Blood and heart were harvested at the end of study.

FIG. 3: Transverse sections of heart depicting the area at risk and infarct staining are presented. Myocardial infarct region stained white (TTC negative), ischemic region stained red, and non-ischemic region stained dark blue. The sum of the infarct size for all 5 slices was used to determine the overall area at risk and ischemic area as a percentage of left ventricle area at risk.

FIG. 4: The effect of albiglutide (1, 3 & 10 mg/kg) on left ventricle infarct size. Left ventricle area at risk following 30 minutes ischemia and 24 hours reperfusion was similar among the groups, indicating that animals were subjected to a similar ischemic insult. Myocardial infarct size presented as % of left ventricle area at risk after 30 minutes ischemia and 24 hours reperfusion. Data are presented as Mean±SEM; *p<0.05 vs. vehicle; **p<0.01 vs. vehicle.

FIG. 5. Recombinant human serum albumin (rHSA) was examined in the cardiac ischemia-reperfusion injury model as an additional control for albiglutide. The dose used was 2.7 mg/kg (dose equivalent to 3 mg/kg albiglutide) and administered as outlined in FIG. 2. Myocardial infarct size was presented as % of left ventricle area at risk after 30 minutes ischemia and 24 hours reperfusion. Data are presented as Mean±SEM.

FIG. 6. Body weight change and food consumption measurement over 2 days of albiglutide dosing at 1, 3, or 10 mg/kg prior to myocardial ischemia-reperfusion injury. Data are presented as Mean±SEM; **p<0.01 vs. vehicle.

FIG. 8: In vivo 2-deoxyglucose experiment schematic protocol.

FIG. 9: Daily body weight change during the experimental protocol is shown. Data are presented as mean±SEM. ***P<0.001.

FIG. 10: In vivo cardiac 2-deoxyglucose uptake in hearts of Vehicle and albiglutide treated rats. Data are presented as mean±SEM. *P<0.03

FIG. 11: Ex vivo cardiac glucose metabolism experiment schematic protocol.

FIG. 12: Schematic of the isolated perfused heart preparation (recirculation mode). Glucose and lactate were measured using an Olympus AU 640 analyzer. Glucose uptake=(Glucose$_{initial}$–Glucose$_{terminal}$)×perfusion volume/heart wet weight (g)/time (h). Lactate efflux=(Lactate$_{initial}$ Lactate$_{terminal}$)×perfusion volume/heart wet weight (g)/time (h)

FIG. 13: Glucose uptake and lactate production (efflux) by heart during a 60 min perfusion period in the Langendorff perfused heart setup. Data are presented as mean±SEM. * P<0.05.

FIG. 14: In Vivo Intermediary Glucose Metabolism in Normal Rat Hearts.

FIG. 15: Lactate Disposition Ex Vivo.

FIG. 16: SEQ ID NO.:1; primary sequence of albiglutide.

SUMMARY OF THE INVENTION

Figure 7:
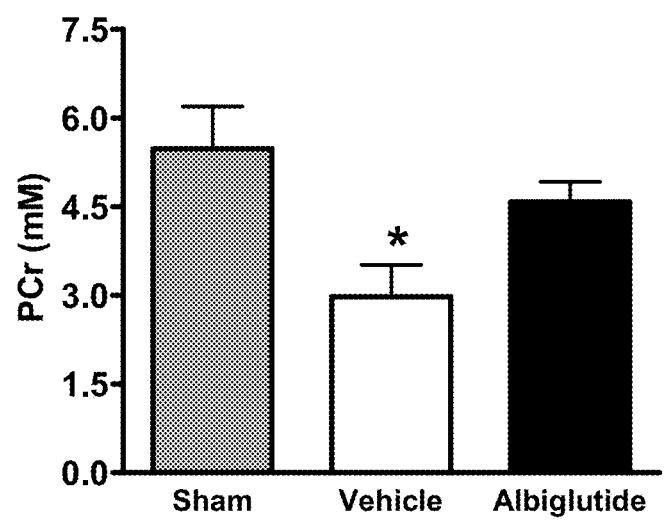
FIG. 7 (A-G). Cardiac function and high energy metabolites

In one embodiment of the present invention, methods are provided for treating, preventing and/or ameliorating at least one cardiovascular disorder in a human comprising administering to said human a pharmaceutical composition comprising at least one polypeptide having at least one GLP-1 activity and/or at least one GLP-1 agonist. In one embodiment, the polypeptide having at least one GLP-1 activity is albiglutide.

In another embodiment, methods are provided for regulating glucose metabolism in cardiac tissue in a human comprising administering a pharmaceutical composition comprising at least one polypeptide having at least one GLP-1 activity and/or at least one GLP-1 agonist to said human in need thereof. In one embodiment, the polypeptide having at least one GLP-1 activity is albiglutide.

In another embodiment, methods are provided for increasing cardiac function in a human in need thereof comprising administering to said human a pharmaceutical composition comprising at least one polypeptide having at least one GLP-1 activity and/or at least one GLP-1 agonist. In one embodiment, the polypeptide having at least one GLP-1 activity is albiglutide.

In another embodiment, methods are provided for reducing infarct size in a human comprising administering a pharmaceutical composition comprising at least one polypeptide having at least one GLP-1 activity and/or at least one GLP-1 agonist. In one embodiment, the polypeptide having at least one GLP-1 activity is albiglutide.

In another embodiment, methods are provided for providing cardiovascular protection to a human comprising administering to said human a pharmaceutical composition comprising albiglutide. In some instances the human has Type II diabetes.

Definitions

"GLP-1 agonist" as used herein means any compound or composition capable of simulating and/or having at least one GLP-1 activity including, but not limited to an incretin hormone and/or fragment, variant and/or conjugate thereof and an incretin mimetic and/or fragment, variant and/or conjugate thereof.

"Incretin hormone" as used herein means any hormone that potentiates insulin secretion or otherwise raises the level or insulin. One example of an incretin hormone is GLP-1.

GLP-1 is an incretin secreted by intestinal L cells in response to ingestion of food. In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying time and slows small bowel motility delaying food absorption. GLP-1 promotes continued beta cell competence by stimulating transcription of genes involved in glucose dependent insulin secretion and by promoting beta-cell neogenesis (Meier, et al. *Biodrugs* 2003; 17 (2): 93-102).

"GLP-1 activity" as used herein means one or more of the activities of naturally occurring human GLP-1, including but not limited to, reducing blood and/or plasma glucose, stimulating glucose-dependent insulin secretion or otherwise raising the level of insulin, suppressing glucagon secretion, reducing fructosamine, increases glucose delivery and metabolism to the brain, delaying gastric emptying, and promoting beta cell competence, and/or neogenesis. Any of these activities and other activity associated with GLP-1 activity may be caused directly or indirectly by a composition having GLP-1 activity or a GLP-1 agonist. By way of example, a composition having GLP-1 activity may directly or indirectly stimulate glucose-dependent insulin secretion while the stimulation of insulin production may indirectly reduce plasma glucose levels in a mammal.

An "incretin mimetic" as used herein is a compound capable of potentiating insulin secretion or otherwise raise the level or insulin. An incretin mimetic may be capable of stimulating insulin secretion, increasing beta cell neogenesis, inhibiting beta cell apoptosis, inhibiting glucagon secretion, delaying gastric emptying and inducing satiety in a mammal. An incretin mimetic may include, but is not limited to, any polypeptide which has GLP-1 activity, including but not limited to, exendin 3 and exendin 4, including any fragments and/or variants and/or conjugates thereof "Hypoglycemic agent" as used herein means any compound or composition comprising a compound capable of reducing blood glucose. A hypoglycemic agent may include, but is not limited to, any GLP-1 agonist including incretin hormones or incretin mimetics, GLP-1 and/or fragment, variant and/or conjugate thereof. Other hypoglycemic agents include, but are not limited to, drugs that increase insulin secretion (e.g., sulfonylureas (SU) and meglitinides, including glipizide, chlorpropamide, glimepiride), inhibit GLP-1 break down (e.g., DPP-IV inhibitors), increase glucose utilization (e.g., glitazones, thiazolidinediones (TZDs) and/or pPAR agonists), reduce hepatic glucose production (e.g., metformin), and delay glucose absorption (e.g., α-glucosidase inhibitors). Examples of sulfonylureas include but are not limited to acetohexamide, chlorpropamide, tolazamide, glipizide, gliclazide, glibenclamide (glyburide), gliquidone, and glimepiride. Examples of glitazones and/or thiazolidinediones include, but are not limited to, rosiglitazone and pioglitazone. Other hypoglycemic agents include but are not limited to, alpha-glucosidase inhibitors (e.g. acarbose, miglitol); dipeptidyl peptidase inhibitors (e.g. sitagliptin, saxagliptin); ergot alkaloids (e.g. bromocriptine); and biquanides (e.g. metformin); meglitinides (e.g. nateglinide, repaglinide); as well as combination medications of the above.

"Polynucleotide(s)" generally refers to any polyribonucleotide or polydeoxyribonucleotide that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques that are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", Meth. Enzymol. (1990) 182:626-646 and Rattan, et al., "Protein Synthesis: Posttranslational Modifications and Aging", Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants may also include, but are not limited to, polypeptides or fragments thereof having chemical modification of one or more of its amino acid side groups. A chemical modification includes, but is not limited to, adding chemical moieties, creating new bonds, and removing chemical moieties. Modifications at amino acid side groups include, without limitation, acylation of lysine-$\epsilon$-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

As used herein "conjugate" or "conjugated" refers to two molecules that are bound to each other. For example, a first polypeptide may be covalently or non-covalently bound to a second polypeptide. The first polypeptide may be covalently bound by a chemical linker or may be genetically fused to the second polypeptide, wherein the first and second polypeptide share a common polypeptide backbone.

As used herein "tandemly oriented" refers to two or more polypeptides that are adjacent to one another as part of the same molecule. They may be linked either covalently or non-covalently. Two or more tandemly oriented polypeptides may form part of the same polypeptide backbone. Tandemly oriented polypeptides may have direct or inverted orientation and/or may be separated by other amino acid sequences.

As used herein, "reduce" or "reducing" blood or plasma glucose refers to a decrease in the amount of blood glucose observed in the blood of a subject after administration a hypoglycemic agent. Reductions in blood or plasma glucose can be measured and assessed per individual or as a mean change for a group of subjects. Additionally, mean reductions in blood or plasma glucose can be measured and assessed for a group of treated subjects as a mean change from baseline and/or as a mean change compared with the mean change in blood or plasma glucose among subjects administered placebo.

As used herein "cardiovascular protection," "cardiac protection" and grammatical derivatives thereof refer to the treatment and/or management of existing cardiovascular disease or disorder as well as the prevention of future cardiovascular disease or disorder and/or prevention of the worsening of cardiovascular symptoms of existing disease or disorder. Cardiovascular protection may be observed, for example, by a lessening of the symptoms of an existing cardviovascular disease or disorder and/or regulation of glucose metabolism in cardiac tissue, increase in cardiac function, improved exercise performance, and/or a reduction in the frequency and/or severity of adverse cardiac events.

As used herein "reducing infarct size" refers to a reduction of the area of coagulation and/or necrosis in cardiovascular tissue due to local ischemia including but not limited to, reducing cardiomyocyte aptoptosis and/or necrosis in the left ventricle in a region distal to the coronary artery occlusion.

As used herein "cardiac agent" refers to any agent which may be administered for the treatment, amelioration or prevention of any cardiovascular disease or disorder. Cardiac agents may include, but are not limited to, one or more of the following agents which may be administered alone or in combination with each other: beta-adrenergic receptor antagonists (including atenolol, bisoprolol, carvedilol, esmolol, labetalol, metoprolol, nadolol, nebivolol, pindolol, propranolol); beta-adrenergic receptor agonists (including dobutamine, dopamine, epinephrine, norepinrphrine, phenylephrine); phosphodiesterase-3 inhibitors (including aminone, milrinone); phosphodiesterase-5 inhibitors (including sildenafil, tadalafil, vardenafil); angiotensin converting enzyme inhibitors (including benazepril, captopril, enalapril, fosinopril, lisinopril, moexipril, quinapril, ramipril, trandolapril); angiotensin receptor blockers (including candesartan, eprosartan, irbesartan, losartan, olmesartan, telmisartan, valsartan); renin antagonists; hydralazine; nitroprusside; nesiritide; ranolazine; cilostazol; calcium channel blockers (including diltiazem, verapamil, amlodipine, nifedipine, nicardipine, felodipine, nislodipine); digoxin; coumadin; heparin; antiplatelet agents (including aspirin, dipyridamole, clopidogrel, prasugrel, ticlopidine); glycoprotein IIb/IIIa antagonists (including abciximab, tirofiban, eptifibatide); thrombolytics (including alteplase, reteplase, streptokinase, urokinase, tenecteplase); spironolactone; diuretics (including furosemide, bumetanide, hydrochlorothiazide, metolazone, acetazolamide, ethacrynic acid); nitrates (including isosorbide dinitrate, isosorbide mononitrate, nitroglycerin); statins (including atorvastatin, fluvastatin, lovastatin, pravastatin, rosuvastatin, simvastatin); ezetimibe; fibrates (including bezfibrate, fenofibrate, gemfibrozil); and anti-arrhythmics (including amiodarone, disopyramide, dronedarone, flecamide, procainamide, propafenone, quinidine, sotalol).

As used herein "enhancing GLP-1 activity" refers to an increase in any and/or all of the activities associated with naturally occurring GLP-1. By way of example, enhancing GLP-1 activity can be measured after administration of at least one polypeptide having GLP-1 activity to a subject and compared with GLP-1 activity in the same subject prior to the administration of the polypeptide having GLP-1 activity or in comparison to a second subject who is administered placebo.

As used herein "diseases associated with elevated blood glucose" include, but are not limited to, type I and type II diabetes, glucose intolerance, hyperglycemia, metabolic disorder, and Alzheimer's disease.

As used herein "co-administration" or "co-administering" as used herein refers to administration of two or more compounds to the same patient. Co-administration of such compounds may be simultaneous or at about the same time (e.g., within the same hour) or it may be within several hours or days of one another. For example, a first compound may be administered once weekly while a second compound is co-administered daily.

As used herein "maximum plasma concentration" or "$C_{max}$" means the highest observed concentration of a substance (for example, a polypeptide having GLP-1 activity or a GLP-1 agonist) in mammalian plasma after administration of the substance to the mammal.

As used herein "Area Under the Curve" or "AUC" is the area under the curve in a plot of the concentration of a substance in plasma against time. AUC can be a measure of the integral of the instantaneous concentrations during a time interval and has the units mass×time/volume, which can also be expressed as molar concentration×time such as nM×day. AUC is typically calculated by the trapezoidal method (e.g., linear, linear-log). AUC is usually given for the time interval zero to infinity, and other time intervals are indicated (for example AUC (t1,t2) where t1 and t2 are the starting and finishing times for the interval). Thus, as used herein "$AUC_{0-24h}$" refers to an AUC over a 24-hour period, and "$AUC_{0-4h}$" refers to an AUC over a 4-hour period.

As used herein "weighted mean AUC" is the AUC divided by the time interval over which the time AUC is calculated. For instance, weighted mean $AUC_{0-24h}$ would represent the $AUC_{0-24h}$ divided by 24 hours.

As used herein "confidence interval" or "CI" is an interval in which a measurement or trial falls corresponding to a given probability p where p refers to a 90% or 95% CI and are calculated around either an arithmetic mean, a geometric mean, or a least squares mean. As used herein, a geometric mean is the mean of the natural log-transformed values back-transformed through exponentiation, and the least squares mean may or may not be a geometric mean as well but is derived from the analysis of variance (ANOVA) model using fixed effects.

As used herein the "coefficient of variation (CV)" is a measure of dispersion and it is defined as the ratio of the standard deviation to the mean. It is reported as a percentage (%) by multiplying the above calculation by 100 (% CV).

As used herein "$T_{max}$" refers to the observed time for reaching the maximum concentration of a substance in plasma of a mammal after administration of that substance to the mammal.

As used herein "serum or plasma half life" refers to the time required for half the quantity of a substance administered to a mammal to be metabolized or eliminated from the serum or plasma of the mammal by normal biological processes.

As used herein "cardiovascular disorder" include, but is not limited to, cardiovascular abnormalities, such as arterio-arterial fistula, arteriovenous fistula, cerebral arteriovenous malformations, congenital heart defects, pulmonary atresia, and Scimitar Syndrome. Congenital heart defects include, but are not limited to, aortic coarctation, cor triatriatum, coronary vessel anomalies, dextrocardia, patent ductus arteriosus, Ebstein's anomaly, Eisenmenger complex, hypoplastic left heart syndrome, dextrocardia, tetralogy of Fallot, transposition of the great vessels, double outlet right ventricle, tricuspid atresia, persistent truncus arteriosus, and heart septal defects, such as aortopulmonary septal defect, endocardial cushion defects, Lutembacher's syndrome, patent foramen ovale, and atrial or ventricular septal defects.

Cardiovascular disorders also include, but are not limited to, chronic cardiac failure, heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, pulmonary edema, cardiac hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, cardiovascular pregnancy complications, Scimitar Syndrome, cardiovascular infection.

Arrhythmias include, but are not limited to, sinus arrhythmia, atrial fibrillation, atrial flutter, bradycardia, extrasystole, Adams-Stokes syndrome, bundle-branch block, sinoatrial block, long QT syndrome, parasystole, Lown-Ganong-Levine syndrome, pre-excitation syndrome, Wolff-Parkinson-White syndrome, sick sinus syndrome, atrial and ventricular tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve diseases include, but are not limited to, aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include, but are not limited to, alcoholic cardiomyopathy, diabetic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemia includes, but is not limited to, coronary artery disease, angina pectoris, coronary aneurysm, coronary arteriosclerosis, coronary thrombosis, coronary vasospasm, myocardial infarction, myocardial stunning, unstable angina, and acute coronary syndrome.

Cardiovascular diseases also include vascular diseases such as aneurysms, angiodysplasia, angiomatosis, bacillary angiomatosis, Hippel-Lindau Disease, Klippel-Trenaunay-Weber syndrome, Sturge-Weber syndrome, angioneurotic edema, aortic diseases, Takayasu's Arteritis, aortitis, Leriche's syndrome, arterial occlusive diseases, arteritis, enarteritis, polyarteritis nodosa, cerebrovascular disorders, diabetic angiopathies, diabetic retinopathy, embolisms, thrombosis, erythromelaigia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Diseases and disorders which may be treated, prevented or amerliorated by a GLP-1 agonist include, but are not limited to: left or right ventricular dysfunction; left or right heart failure; low or high cardiac output; acute decompensated heart failure; chronic congestive heart failure; cardiomyopathy of any cause, including but not limited to cardiomyopathy caused by genetic factors, coronary artery disease, myocardial infarction, structural valve disease, infection, congenital heart disease, hypertension, alcohol consumption, diabetes, left ventricular hypertrophy, myocarditis, amyloidosis, hemochromatosis, glycogen storage disease, metabolic disorders, disorders of glucose or lipid metabolism, inflammatory disorders; coronary artery disease; myocardial ischemia; acute myocardial infarction; acute coronary syndrome or unstable angina pectoris; pulmonary edema; left or right ventricular hypertrophy; cardiac arrest; myocarditis; skeletal muscle dysfunction or skeletal myopathy, including but not limited to that caused by genetic factors, peripheral vascular disease, cachexia, cancer, chronic heart failure, chronic lung disease, inflammatory disorders; impaired exercise capacity; and/or peripheral vascular disease.

DETAILED DESCRIPTION OF THE INVENTION

In one embodiment of the present invention, methods are provided for treating, preventing and/or ameliorating at least one cardiovascular disorder in a human comprising administering to said human a pharmaceutical composition comprising at least one polypeptide having at least one GLP-1 activity and/or at least one GLP-1 agonist. In another embodiment, methods are provided for regulating glucose metabolism in cardiac tissue in a human comprising administering a pharmaceutical composition comprising at least one polypeptide having at least one GLP-1 activity and/or at least one GLP-1 agonist to said human in need thereof. In another embodiment, methods are provided for increasing cardiac function in a human in need thereof comprising administering to said human a pharmaceutical composition comprising at least one polypeptide having at least one GLP-1 activity and/or at least one GLP-1 agonist. In another embodiment, methods are provided for reducing infarct size in a human comprising administering a pharmaceutical composition comprising at least one polypeptide having at least one GLP-1 activity and/or at least one GLP-1 agonist. In one embodiment, the polypeptide having at least one GLP-1 activity is albiglutide.

As is understood in the art, "heart failure" defines a clinical syndrome with many different etiologies or disease manifestations. Typically, congestive heart failure, refers to increase in pulmonary venous pressure resulting from the inability of the heart to discharge its contents normally and leading to pulmonary and systemic congestion. This condition can be caused by many different pathological process that can lead to impairment of cardiac function including but not to genetic factors, coronary artery disease, myocardial infarction, structural valve disease, infection, congenital heart disease, hypertension, alcohol consumption, diabetes, left ventricular hypertrophy, myocarditis, amyloidosis, hemochromatosis, glycogen storage disease, metabolic disorders, disorders of glucose or lipid metabolism, and/or inflammatory disorders. The present invention describes methods for addressing depressed myocardial function, by increasing glucose efficiency and ventricular contractility. Thus, the methods of the present invention can be used for treatment, prevention and/or amelioration of a number of cardiovascular disease described herein.

In one aspect of the invention, the GLP-1 agonist comprises SEQ ID NO:1. As is used herein SEQ ID NO:1 is the primary polypeptide sequence of albiglutide (See FIG. 16).

An embodiment of the invention comprises a GLP-1 agonist that may be, but is not limited to, GLP-1 or a fragment, variant, and/or conjugate thereof. GLP-1 fragments and/or variants and/or conjugates of the present invention typically have at least one GLP-1 activity. A GLP-1 or a fragment, variant, and/or conjugate thereof may comprise human serum albumin. Human serum albumin may be conjugated to the GLP-1 or fragment and/or variant thereof. Human serum albumin may be conjugated to an incretin hormone (such as GLP-1) and/or incretin mimetic (such as exendin 3 and exendin 4) and/or fragments and/or variants thereof through a chemical linker prior to injection or may be chemically linked to naturally occurring human serum albumin in vivo (see for instance, U.S. Pat. No. 6,593,295 and U.S. Pat. No. 6,329,336, herein incorporated by reference in their entirety). Alternatively, human serum albumin may be genetically fused to a GLP-1 and/or fragment and/or variant thereof or other GLP-1 agonist such as exendin-3 or exendin-4 and/or fragments and/or variants thereof. Examples of GLP-1 and fragments and/or variants thereof genetically fused with human serum albumin are provided in the following PCT applications: WO 2003/060071, WO 2003/59934, WO 2005/003296, WO 2005/077042 (herein incorporated by reference in their entirety).

Polypeptides having GLP-1 activity or GLP-1 agonists may comprise at least one fragment and/or variant of human GLP-1. The two naturally occurring fragments of human GLP-1 are represented in SEQ ID NO: 2.

```
                                          (SEQ ID NO.: 2)
 7   8   9  10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Xaa
``` wherein: Xaa at position 37 is Gly (hereinafter designated as "GLP-1(7-37)"), or —NH$_2$ (hereinafter designated as "GLP-1(7-36)"). GLP-1 fragments may include, but are not limited to, molecules of GLP-1 comprising, or alternatively consisting of, amino acids 7 to 36 of human GLP-1 (GLP-1(7-36)). Variants of GLP-1 or fragments thereof may include, but are not limited to, one, two, three, four, five or more amino acid substitutions in wild type GLP-1 or in the naturally occurring fragments of GLP-1 shown in SEQ ID NO.: 2. Variants GLP-1 or fragments of GLP-1 may include, but are not limited to, substitutions of an alanine residue analogous to alanine 8 of wild type GLP-1, such alanine being mutated to a glycine (hereinafter designated as "A8G") (See for example, the mutants disclosed in U.S. Pat. No. 5,545,618, herein incorporated by reference in its entirety).

In some aspects, at least one fragment and variant of GLP-1 comprises GLP-1(7-36(A8G)) and is genetically fused to human serum albumin. In a further embodiment, polypeptides of the invention comprise one, two, three, four, five, or more tandemly oriented molecules of GLP-1 and/or fragments and/or variants thereof fused to the N- or C-terminus of human serum albumin or variant thereof. Other embodiments have such A8G polypeptides fused to the N- or C-terminus of albumin or variant thereof. An example of two tandemly oriented GLP-1(7-36)(A8G) fragments and/or variants fused to the N-terminus of human serum albumin comprises SEQ ID NO:1, which is presented in FIG. 16. In another aspect, at least one fragment and variant of GLP-1 comprises at least two GLP-1(7-36(A8G)) tandemly and genetically fused to the human serum albumin.

At least two GLP-1(7-36(A8G)) may be genetically fused at the N-terminus of the human serum albumin. At least one polypeptide having GLP-1 activity may comprise SEQ ID NO.: 1. In some aspects the least one polypeptide having GLP-1 activity is albiglutide.

Variants of GLP-1(7-37) may be denoted for example as Glu$^{22}$-GLP-1(7-37)OH which designates a GLP-1 variant in which the glycine normally found at position 22 of GLP-1(7-37)OH has been replaced with glutamic acid; Val$^8$-Glu$^{22}$-GLP-1(7-37)OH designates a GLP-1 compound in which alanine normally found at position 8 and glycine normally found at position 22 of GLP-1(7-37)OH have been replaced with valine and glutamic acid, respectively. Examples of variants of GLP-1 include, but are not limited to,

| | | |
|---|---|---|
| Val$^8$-GLP-1(7-37)OH | Gly$^8$-GLP-1(7-37)OH | Glu$^{22}$-GLP-1(7-37)O-H |
| Asp$^{22}$-GLP-1(7-37)OH | Arg$^{22}$-GLP-1(7-37)OH | Lys$^{22}$-GLP-1(7-37)OH |
| Cys$^{22}$-GLP-1(7-37)OH | Val$^8$-Glu$^{22}$-GLP-1(7-37)OH | Val$^8$-Asp$^{22}$-GLP-1(7-37)OH |
| Val$^8$-Arg$^{22}$-GLP-1(7-37)OH | Val$^8$-Lys$^{22}$-GLP-1(7-37)OH | Val$^8$-Cys$^{22}$-GLP-1(7-37)OH |
| Gly$^8$-Glu$^{22}$-GLP-1(7-37)OH | Gly$^8$-Asp$^{22}$-GLP-1(7-37)OH | Gly$^8$-Arg$^{22}$-GLP-1(7-37)OH |
| Gly$^8$-Lys$^{22}$-GLP-1(7-37)OH | Gly$^8$-Cys$^{22}$-GLP-1(7-37)OH | Glu$^{22}$-GLP-1(7-36)OH |
| Asp$^{22}$-GLP-1(7-36)OH | Arg$^{22}$-GLP-1(7-36)OH | Lys$^{22}$-GLP-1(7-36)OH |
| Cys$^{22}$-GLP-1(7-36)OH | Val$^8$-Glu$^{22}$-GLP-1(7-36)OH | Val$^8$-Asp$^{22}$-GLP-1(7-36)OH |

-continued

Val$^8$-Arg$^{22}$-GLP-1(7-36)OH
Val$^8$-Lys$^{22}$-GLP-1(7-36)OH
Val$^8$-Cys$^{22}$-GLP-1(7-36)OH

Gly$^8$-Glu$^{22}$-GLP-1(7-36)OH
Gly$^8$-Asp$^{22}$-GLP-1(7-36)OH
Gly$^8$-Arg$^{22}$-GLP-1(7-36)OH

Gly$^8$-Lys$^{22}$-GLP-1(7-36)OH
Gly$^8$-Cys$^{22}$-GLP-1(7-36)OH
Lys$^{23}$-GLP-1(7-37)OH

Val$^8$-Lys$^{23}$-GLP-1(7-37)OH
Gly$^8$-Lys$^{23}$-GLP-1(7-37)OH
His$^{24}$-GLP-1(7-37)OH

Val$^8$-His$^{24}$-GLP-1(7-37)OH
Gly$^8$-His$^{24}$-GLP-1(7-37)OH
Ly$^{s24}$-GLP-1(7-37)OH

Val$^8$-Lys$^{24}$-GLP-1(7-37)OH
Gly$_8$-Lys$^{23}$-GLP-1(7-37)OH
Glu$^{30}$-GLP-1(7-37)OH

Val$^8$-Glu$^{30}$-GLP-1(7-37)OH
Gly$^8$-Glu$^{30}$-GLP-1(7-37)OH
Asp$^{30}$-GLP-1(7-37)OH

Val$^8$-Asp$^{30}$-GLP-1(7-37)OH
Gly$^8$-Asp$^{30}$-GLP-1(7-37)OH
Gln$^{30}$-GLP-1(7-37)OH

Val$^8$-Gln$^{30}$-GLP-1(7-37)OH
Gly$^8$-Gln$^{30}$-GLP-1(7-37)OH
Tyr$^{30}$-GLP-1(7-37)OH

Val$^8$-Tyr$^{30}$-GLP-1(7-37)OH
Gly$^8$-Tyr$^{30}$-GLP-1(7-37)OH
Ser$^{30}$-GLP-1(7-37)OH

Val$^8$-Ser$^{30}$-GLP-1(7-37)OH
Gly$^8$-Ser$^{30}$-GLP-1(7-37)OH
His$^{30}$-GLP-1(7-37)OH

Val$^8$-His$^{30}$-GLP-1(7-37)OH
Gly$^8$-His$^{30}$-GLP-1(7-37)OH
Glu$^{34}$-GLP-1(7-37)OH

Val$^8$-Glu$^{34}$-GLP-1(7-37)OH
Gly$^8$-Glu$^{34}$-GLP-1(7-37)OH
Ala$^{34}$-GLP-1(7-37)OH

Val$^8$-Ala$^{34}$-GLP-1(7-37)OH
Gly$^8$-Ala$^{34}$-GLP-1(7-37)OH
Gly$^{34}$-GLP-1(7-37)OH

Val$^8$-Gly$^{34}$-GLP-1(7-37)OH
Gly$^8$-Gly$^{34}$-GLP-1(7-37)OH
Ala$^{35}$-GLP-1(7-37)OH

Val$^8$-Ala$^{35}$-GLP-1(7-37)OH
Gly$^8$-Ala$^{35}$-GLP-1(7-3 )OH
Lys$^{35}$-GLP-1(7-37)OH

Val$^8$-Lys$^{35}$-GLP-1(7-37)OH
Gly$^8$-Lys$^{35}$-GLP-1(7-37)OH
His$^{35}$-GLP-1(7-37)OH

Val$^8$-His$^{35}$-GLP-1(7-37)OH
Gly$^8$-His$^{35}$-GLP-1(7-37)OH
Pro$^{35}$-GLP-1(7-37)OH

Val$^8$-Pro$^{35}$-GLP-1(7-37)OH
Gly$^8$-Pro$^{35}$-GLP-1(7-37)OH
Glu$^{35}$-GLP-1(7-37)OH

Gly$^8$-Glu$^{35}$-GLP-1(7-37)OH
Val$^8$-Ala$^{27}$-GLP-1(7-37)OH
Val$^8$-His$^{37}$-GLP-1(7-37)OH

Val$^8$-Glu$^{22}$-Lys$^{23}$-GLP-1(7-37)OH
Val$^8$-Glu$^{22}$-Glu$^{23}$-GLP-1(7-37)OH
Val$^8$-Glu$^{22}$-Ala$^{27}$-GLP-1(7-37)OH

Val$^8$-Gly$^{34}$-Lys$^{35}$-GLP-1(7-37)OH
Val$^8$-His$^{37}$-GLP-1-(7-37)OH
Gly$^8$-His$^{37}$-GLP-1(7-37)OH

Val$^8$-Glu$^{22}$-Ala$^{27}$-GLP-1(7-37)OH
Gly$^8$-Glu$^{22}$-Ala$^{27}$-GLP-1(7-37)OH
Val$^8$-Lys$^{22}$-Glu$^{23}$-GLP-1(7-37)OH

Gly$^8$-Lys$^{22}$-Glu$^{23}$-GLP-1(7-37)OH.
Val$^8$-Glu$^{35}$-GLP-1(7-37)OH

Variants of GLP-1 may also include, but are not limited to, GLP-1 or GLP-1 fragments having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

GLP-1 fragments or variants may also include polypeptides in which one or more amino acids have been added to the N-terminus and/or C-terminus of GLP-1(7-37)OH of said fragment or variant. The amino acids in GLP-1 in which amino acids have been added to the N-terminus or C-terminus are denoted by the same number as the corresponding amino acid in GLP-1(7-37)OH. For example, the N-terminus amino acid of a GLP-1 compound obtained by adding two amino acids to the N-terminus of GLP-1(7-37)OH is at position 5; and the C-terminus amino acid of a GLP-1 compound obtained by adding one amino acid to the C-terminus of GLP-1(7-37)OH is at position 38. Thus, position 12 is occupied by phenylalanine and position 22 is occupied by glycine in both of these GLP-1 compounds, as in GLP-1(7-37)OH. Amino acids 1-6 of a GLP-1 with amino acids added to the N-terminus may be the same as or a conservative substitution of the amino acid at the corresponding position of GLP-1(1-37)OH. Amino acids 38-45 of a GLP-1 with amino acids added to the C-terminus may be the same as or a conservative substitution of the amino acid at the corresponding position of glucagon or exendin-4.

A skilled artisan will understand the various methods for measuring and calculating the pharmacokinetic (for example, but not limited to, Cmax, AUC, Tmax, serum half-life) and pharmacodynamic (for example, but not limited to, serum, plasma and blood glucose levels) parameters described herein. Furthermore, the skilled artisan will understand the various methods for making statistical comparisons (for example, but not limited to, comparisons of change from baseline to post-treatment and/or comparisons among treatment groups) and/or analysis of the pharmacokinetic and pharmacodynamic parameters described herein. Furthermore, the skilled artisan will understand and be able to employ various other methods for collecting and analyzing pharmacokinetic, pharmacodynamic and other clinical data.

As is understood in the art pharmaceutical compositions of the present invention can be administered subcutaneously. A subcutaneous injection can be administered as a single shot, for example, but not limited to, at a volume of about 0.01 mL to about 5.0 mL per injection. Alternatively, a subcutaneous injection can be administered continuously. Additionally, subcutaneous injections can be administered as a combination of single and continuous injections and as a combination of subcutaneous and other routes of administration. The pharmaceutical compositions of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration. In some aspects said pharmaceutical composition comprises less than about 4.0 mg of SEQ ID NO:1 per dose, including but not limited to 3.75 mg/ml. In another aspect, said pharmaceutical composition comprises less than about 2.0 mg of SEQ ID NO:1 per dose, including but not limited to 1.88 mg/ml. The pharmaceutical composition may be administered at a low dose once every week. For example, a pharmaceutical composition comprising albiglutide could be administered once weekly by injection in an amount of about 0.25 mg, 0.5 mg, 0.75 mg, 1.0 mg, 1.25 mg, 1.5 mg, 1.75 mg, 1.88 mg, 2.0 mg, 2.25 mg, 2.5 mg, 2.75 mg, 3.0 mg, 3.25 mg, 3.5 mg, 3.75 mg, 4.0 mg, 15 mg, or 30 mg. The pharmaceutical compositions of the present invention may be administered, for example, weekly over a period of 6 months or less. Alternatively, it may be administered, for example, weekly over a longer period or chronically. In some aspects the pharmaceutical compositions may be administered as at least one bolus injection.

In another aspect, the pharmaceutical composition decreases the amount of cardiac lactate efflux in said human. Pharmaceutical composition of the present invention can be co-administered with at least one second cardiac agent. As is understood in the art, cardiac agents include but are not limited to, antianginal agents such as nitrates, beta blockers, ACE inhibitors, angiontensin II receptor blockers, diuretics, vasodilators, beta-adrenergic receptor antagonists, beta-adrenergic receptor agonists, phosphodiesterase-3 inhibitors, phosphodiesterase-5 inhibitors, angiotensin converting enzyme inhibitors, angiotensin receptor blockers, renin antagonists; hydralazine; nitroprusside; nesiritide; ranolazine; cilostazol; calcium channel blockers, digoxin; coumadin; heparin; antiplatelet agents, glycoprotein IIb/IIIa antagonists, thrombolytics, spironolactone; diuretics, nitrates, statins, ezetimibe; fibrates and/or anti-arrhythmics.

In another aspect, methods are provided wherein the pharmaceutical composition improves cardiac function in said human. In other aspects, the pharmaceutical composition increases vascular dilation and/or increases NO production or availability in said human.

In one embodiment, the human has a chronic cardiac condition. In another aspect, the human has an acute cardiac condition. The methods of the present invention also provide for treatment of humans who have both a chronic and acute cardiac condition or are at risk of one or the other or both. In some instances the human has ischemic congestive heart failure. In another example, the human has non-ischemic congestive heart failure. In some embodiments, the human has acute myocardial infarction (AMI).

The present invention also provides methods wherein the human has at least one disease selected from the group of: chronic cardiac failure, heart disease, arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, pulmonary edema, cardiac hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis, pneumopericardium, postpericardiotomy syndrome, pulmonary heart disease, rheumatic heart disease, ventricular dysfunction, hyperemia, cardiovascular pregnancy complications, Scimitar syndrome, cardiovascular syphilis, cardiovascular tuberculosis, alcoholic cardiomyopathy, diabetic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns syndrome, myocardial reperfusion injury, myocarditis, coronary disease, such as angina pectoris, coronary aneurysm, coronary arteriosclerosis, coronary thrombosis, coronary vasospasm, myocardial infarction, myocardial stunning, vascular diseases such as aneurysms, angiodysplasia, angiomatosis, bacillary angiomatosis, Hippel-Lindau Disease, Klippel-Trenaunay-Weber Syndrome, Sturge-Weber syndrome, angioneurotic edema, aortic diseases, Takayasu's arteritis, aortitis, Leriche's syndrome, arterial occlusive diseases, arteritis, enarteritis, polyarteritis nodosa, cerebrovascular disorders, diabetic angiopathies, diabetic retinopathy, embolisms, thrombosis, erythromelaigia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

In one embodiment, the human has at least one of the following diseases or disorders: left or right ventricular dysfunction; left or right heart failure; low or high cardiac output; acute decompensated heart failure; chronic congestive heart failure; cardiomyopathy of any cause, including, but not limited to, cardiomyopathy caused by genetic factors, coronary artery disease, myocardial infarction, structural valve disease, infection, congenital heart disease, hypertension, alcohol consumption, diabetes, left ventricular hypertrophy, myocarditis, amyloidosis, hemochromatosis, glycogen storage disease, metabolic disorders, disorders of glucose or lipid metabolism, inflammatory disorders; coronary artery disease; myocardial ischemia; acute myocardial infarction; acute coronary syndrome or unstable angina pectoris; pulmonary edema; left or right ventricular hypertrophy; cardiac arrest; myocarditis; skeletal muscle dysfunction or skeletal myopathy, including but not limited to that caused by genetic factors, peripheral vascular disease, cachexia, cancer, chronic heart failure, chronic lung disease, inflammatory disorders; impaired exercise capacity; peripheral vascular disease.

In other embodiments, the human has Type II diabetes. The human may have hyperglycemia or may be diagnosed as pre-diabetic or at risk of developing diabetes. The pharmaceutical compositions of the present invention also improve at least one of the following functions in said human: myocardial glucose utilization, myocardial efficiency, left ventricular function, and/or exercise capacity.

The present invention also provides use of at least one polypeptide having GLP-1 activity and/or at least one GLP-1 agonist in the manufacture of a medicament for the treatment of at least one cardiovascular disease or disorder as described herein. The present invention also provides for any use of at least one polypeptide having GLP-1 activity and/or at least one GLP-1 agonist as described herein, including but not limited to, use of a GLP-1 agonist to treat, prevent and/or ameliorate: left or right ventricular dysfunction; left or right heart failure; low or high cardiac output; acute decompensated heart failure; chronic congestive heart failure; cardiomyopathy of any cause, including but not limited to cardiomyopathy caused by genetic factors, coronary artery disease, myocardial infarction, structural valve disease, infection, congenital heart disease, hypertension, alcohol consumption, diabetes, left ventricular hypertrophy, myocarditis, amyloidosis, hemochromatosis, glycogen storage disease, metabolic disorders, disorders of glucose or lipid metabolism, inflammatory disorders; coronary artery disease; myocardial ischemia; acute myocardial infarction; acute coronary syndrome or unstable angina pectoris; pulmonary edema; left or right ventricular hypertrophy; cardiac arrest; myocarditis; skeletal muscle dysfunction or skeletal myopathy, including but not limited to that caused by genetic factors, peripheral vascular disease, cachexia, cancer, chronic heart failure, chronic lung disease, inflammatory disorders; impaired exercise capacity; and/or peripheral vascular disease. In one embodiment, the polypeptide having at least one GLP-1 activity is albiglutide.

In one embodiment, methods are provided for providing cardiovascular protection to a human comprising administering to said human a pharmaceutical composition comprising albiglutide. In some aspects, the pharmaceutical composition comprises about 3.75 mg, 15 mg or 30 mg of albiglutide. In other aspects, the pharmaceutical composition comprises about 4 mg or less of albiglutide. The pharmaceutical composition may comprises albiglutide in an amount selected from: 0.25 mg, 0.5 mg, 0.75 mg, 1.0 mg, 1.25 mg, 1.5 mg, 1.75 mg, 1.88 mg, 2.0 mg, 2.25 mg, 2.5 mg, 2.75 mg, 3.0 mg, 3.25 mg, 3.5 mg, 3.75 mg, 4.0 mg, 15 mg, 30 mg per dose. The pharmaceutical composition comprising albiglutide may be delivered by subcutaneous injection which may be administered once a week.

The present invention provides the use of a pharmaceutical composition comprising albiglutide in an amount selected from: 1 mg, 0.25 mg, 0.5 mg, 0.75 mg, 1.0 mg, 1.25 mg, 1.5 mg, 1.75 mg, 1.88 mg, 2.0 mg, 2.25 mg, 2.5 mg, 2.75 mg, 3.0 mg, 3.25 mg, 3.5 mg, 3.75 mg, 4.0 mg, 15 mg, and 30 mg in a single dose for providing cardiovascular protection. In some instances, the cardiovascular protection is provided to a human.

Also provided herein are methods for increasing gene expression of at least one gene associated with glycolysis and glycogenesis including, but not limited to, ALDOC, CPT1B, IGF1R, PDHA1, GSK3B, GYS1, SLC2A1. In some instances gene expression is increased in the non-ischemic region of an I/R heart following treatment with albiglutide. In some instances, gene expression of at least one of the following genes: ACSL1, CPT1B, GAPDH, IGF1R, SLC2A4, HK2, GYS1, ESSRA, HIF1A, PPARGC1A, PDHA1, ALDOC, GSK3B, and AKT1 is increased after administration of a pharmaceutical composition comprising albiglutide.

EXAMPLES

The following examples illustrate various non-limiting aspects of this invention.

Example 1

Preclinical Evaluation of Albiglutide on Cardiac Function in Myocardial Ischemia Model In the present study, we hypothesized that albiglutide may exert cardioprotective effects in a rodent model of myocardial ischemia-reperfusion injury. The rat myocardial ischemia-reperfusion injury model is a clinically relevant and translatable animal model.

It also is a widely used model for initial testing of compounds for potential heart failure therapy. GLP-1 (7-36 and 9-36) and like mimetics (exendin-4 and liraglutide) have all been shown to be cardioprotective in a rodent model of ischemia-reperfusion injury.

Male Sprague-Dawley rats (~300 g body weight) were used for the study. The following 5 study groups were included in the study:

Group 1: Vehicle (ischemia/reperfusion injury rats treated with vehicle); n=8-10
Group 2: rHSA (ischemia/reperfusion injury rats treated with rHSA); n=8-10
Group 3: Albiglutide (ischemia/reperfusion injury rats treated with albiglutide, 1 mg/kg); n=8-10
Group 4: Albiglutide (ischemia/reperfusion injury rats treated with albiglutide, 3 mg/kg); n=8-10
Group 5: Albiglutide (ischemia/reperfusion injury rats treated with albiglutide, 10 mg/kg); n=8-10

Experimental Protocol(s)

Myocardial ischemia-reperfusion (I/R) injury was performed under anesthesia (Nembutal, 60 mg/kg, IP). Non-fasted rats were subjected to open-chest surgery and myocardial I/R injury was induced by occlusion of left anterior descending (LAD) artery for 30 minutes followed by 24 hour reperfusion. Rats were pre-treated with vehicle, recombinant human albumin (rHSA), or albiglutide for 3 days as shown in FIG. 2. Rats were administered with rHSA at the dose of 2.7 mg/kg by subcutaneous injection at 48 hours, 24 hours and 2 hours before ischemia then subjected to 30 minute ischemia and 24 hour reperfusion. Other rats were administered with albiglutide at a dose of 1 mg/kg, 3 mg/kg or 10 mg/kg by subcutaneous injection at 48 hours, 24 hours and 2 hours before ischemia then subjected to 30 minutes ischemia and 24 hours reperfusion. Blood samples were collected immediately before ischemia and 24 hours after reperfusion (FIG. 2).

Cardiac function was assessed after the 30 minutes ischemia and 24 hours reperfusion insult using a 1.8 F Millar Mikro-Tip pressure catheter transducer inserted into the left ventricle through the right carotid artery.

At the end of study, rat hearts were harvested and perfused with 1% triphenyltetrazolium chloride (TTC) phosphate buffer solution to delineate necrotic and viable myocardium. The LAD artery was subsequently retied at the site of previous occlusion and the heart was perfused with Evans Blue dye to delineate the area at risk and the non-ischemic area. The hearts were transversely cut into five sections and the sections were photographed using a digital camera. Infarct size and area at risk were determined using Image-Pro Plus.

Insulin was measured using an MDS rat insulin kit. Blood glucose and lactate were determined using an Olympus AU640 clinical chemistry analyzer.

Hemodynamic Measurement and Postmortem Analysis

At the end of the FR study (24 hr post-reperfusion), animals were anesthetized with isoflurane (2% in oxygen) and a 2 F Millar Mikro-tip catheter transducer was inserted into the left ventricle through the right carotid artery to measure left ventricular pressure and the derived peak positive and negative change in pressure ($+dP/dt_{max}$ and $-dP/dt_{min}$, respectively) as reported previously (18,19). After hemodynamic measurements, the heart was excised and perfused with saline to wash out the residual blood through an aortic cannula (18-gauge needle). To delineate infarcted tissues from viable myocardium, the heart was then perfused with a 1% solution of 2,3,5-triphenyltetrazolium chloride (TTC) in phosphate buffer (pH 7.4, 37° C.). The viable myocardium stained red, and the infarcted myocardium stained white. To delineate the area at risk (ischemic area), the coronary artery was then tied at the site of the previous occlusion and the aortic root was perfused with a 1% Evans blue dye (Sigma) in normal saline. As a result of this procedure, the portion of the LV supplied by the previously occluded coronary artery (area at risk) was identified by the absence of blue dye, whereas the rest of the LV was stained dark blue. The heart was frozen, after which all atrial and right ventricular tissues were excised. The LV was cut into transverse slices, which were photographed using a digital camera. The borders of the infarct, ischemic and nonischemic area of heart image were traced and measured using Image-Pro Plus and from these measurements infarct size was calculated as a percentage of the ischemic area. Ischemic area was calculated as a percentage of LV area.

In Vivo Cardiac Energetics Assessment

To examine the effect of albiglutide on the cardiac energetic profile (e.g. ATP, PCr, ATP/PCr) following cardiac I/R injury, rats were treated with vehicle or albiglutide (10 mg/kg/day for 3 days) as described above (n=10 per group). Rats were subjected to 30 min of ischemia followed by 24 h reperfusion; sham-operated rats were included in this study as control (n=5). At 24 h post-reperfusion, rats were anaesthetized with 2.0% isoflurane (Abbott Laboratories, Chicago, Ill.) for the magnetic resonance imaging (MRI)/spectroscopy (MRS) experiments. All in vivo MRI/S experiments were performed using a double tune ($^1$H, $^{31}$P) concentric surface radio frequency (RF) coil setup on a 9.4T/30 cm Bruker Biospec system (Billerica, Mass.). The concentric surface RF coil (M2M Imaging Corp, OH) design consisted of an outer $^1$H butterfly coil (35 mm) tuned to 400.44 MHz and an inner $^{31}$P circular coil (25 mm) tuned to 162.10 MHz. Following a tripilot gradient-echo image, short-axis cardiac images were acquired using a retrospectively cardiac gated fast low angle shot (FLASH) sequence. A cine loop was generated for each imaging slice through the ventricles with a sufficient number of delays to cover the cardiac cycle. The imaging parameters were as follows: matrix dimensions, 128×128; TR/TE, 7/1.5 ms; slice thickness, 2.0 mm; FOV, 5.0 cm; number of repetition 250; cine loop, 10 images. Left ventricle (LV) functional parameters were analyzed (Analyze AVW software, Analyze-Direct, Lenexa, Kans.). $^{31}$P MRS was performed immediately following the imaging using the same RF hardware and spatially localized spectroscopy of the heart was performed using a 3-D Image Selected In Vivo Spectroscopy (ISIS) sequence with outer volume suppression (TR=4 s, NS=512, SW=10 kHz, 1 k data). The spectroscopic voxel of interest size was 15.8×11×17 mm and positioned to cover the LV in an oblique plane in all three orthogonal directions. $^{31}$P NMR spectra were processed using an exponential filter and baseline flattening. The phosphocreatine (PCr) peak, was set to 0 ppm, and the inorganic phosphate (P) peaks at ~4.9-5.3 ppm (including both intracellular and extracellular P) and the β-adenosine triphosphate (ATP) peak at −16 ppm were integrated in order to calculate the PCr/P, and PCr/ATP ratios respectively (Nuts NMR processing software, Acorn NMR Inc., Fremont, Calif.). The intracellular pH was calculated using the chemical shift difference between intracellular Pi and PCr as previously described (Taylor, et al., *Magn Reson Med* 1986 February; 3(1):44-54).

Cardiac Metabolic Gene Expression Analysis

Quantitative TaqMan reverse-transcription (RT) polymerase chain reaction (PCR) analysis was performed on total RNA that was extracted from LV in a subgroup of SD rats that were treated with vehicle or albiglutide (10 mg/kg/day for 3 days) as described above (n=8 per group). Twenty four key metabolic, mitochondrial, and stress associated genes were assessed in normal LV as well as ischemic and non-ischemic LV from I/R experiment. These genes consisted of: ACSL1, CPT1B, GAPDH, IGF1R, SLC2A4, HK2, GYS1, ESSRA, HIF1A, PPARGC1A, PDHA1, ALDOC, GSK3B, AKT1, SLC2A1, PYGL, PRKAA2, PPARG, HK1, PDK1, UCP2, ACTB, LDHA, UCP3. Gene expression data was normalized using the Omics Studio® software. One-way ANAOVA and PCA were performed thereafter.

Statistical Analysis

Data are presented as mean±SEM. Differences between groups were compared by paired and unpaired Student's t tests or by a one-way ANOVA followed by a Bonferroni test for multiple comparisons. A p value of <0.05 was considered statistically significant.

Sample Collection:

Blood samples were collected at baseline (pre-ischemia) and 24 hours after reperfusion using EDTA tubes.

Animal Diet: Normal rodent diet

The following drug material was used in the study:
1) Albiglutide
2) rHSA (recombinant human serum albumin)
3) Vehicle (10 mM Sodium Phosphate, 153 mM Mannitol, 117 mM Trehalose, 0.01% (w/v) Polysorbate 80, pH 7.2). Rats were administered with the dose of 1 ml/kg by subcutaneous injection at 48 hours, 24 hours and 2 hours before ischemia then subjected to a 30 minutes ischemia and 24 hours reperfusion.

Preparation Vehicle/Drug/Reagents:

Approximately 900 mL of HPLC grade water was added to a beaker. A clean stir bar was added and the following were mixed on a magnetic stir plate: 0.41±0.01 g of sodium phosphate monobasic monohydrate, 0.99±0.01 g sodium phosphate dibasic anhydrous, 44.26±0.1 g D-trehalose dehydrate, 27.87±0.1 g mannitol, and 10 mL of a 1% Polysorbate 80 stock solution. pH was measured and, if necessary, the pH was adjusted to 7.2 using 1N sodium hydroxide or phosphoric acid. The solution was transferred to a 1000 mL volumetric flask and HPLC grade water was added until the final volume of 1000 mL was reached before stirring for at least 20 minutes. The buffer was filtered through a 0.2 micron filter unit assembly. The flask was stored at 4° C. protected from light by wrapping the flask in aluminium foil. The rHSA powder stored in −20° C. freezer was dissolved in vehicle to a concentration of 2.7 mg/ml as a dosing solution. Stock solution (131 mg/ml) stored in −80° C. freezer was diluted with vehicle to the working solution of 3 mg/ml or 30 mg/ml albiglutide.

Albiglutide Pharmacokinetics Analysis in SD Rat

Sample Collection:

In a separate group of SD rats (n=4), a PK study was performed in order to obtain Cmax, AUC, t1/2, etc. for albiglutide (15 mg/kg, S.C.). Blood samples were collected at 0, 0.5, 1, 3, 6, 8, and 24 hours post-treatment using EDTA tubes (250 μl/tube).

Analytical Methods:

Rat plasma samples were analyzed for albiglutide using an analytical method based on sample dilution, followed by immunoassay analysis. The lower limit of quantification (LLQ) for albiglutide was 100 ng/mL using a 100 μL aliquot of rat plasma with a higher limit of quantification (HLQ) of 2500 ng/mL. The computer systems that were used on this study to acquire and quantify data included Wallac 1420 Workstation Version 3.0 Revision 5 and SMS2000 version 2.1. The applicable analytical runs met all predefined run acceptance criteria.

Data Analysis

Data are presented as mean±SEM. Differences between groups were compared by paired and unpaired Student's t tests or by ANOVA followed by a Bonferroni test for multiple comparisons. P values of <0.05 were considered statistically significant.

Results

Initially, blood pharmacokinetics was assessed after single s.c. dose of albiglutide, 15 mg/kg. The cardioprotection study doses were chosen based off of modelling of 1, 3, and 10 mg/kg dosing and comparing with clinical doses achieved with albiglutide. FIG. 1 illustrates the actual blood concentrations assessed during the pk study as well as the modelling of the 15 mg/kg dose.

For the cardioprotection study, animals were dosed at 48 hours, 24 hours, and 2 hours prior to I/R injury (FIG. 2). The left anterior descending coronary artery was occluded for 30 minutes prior to 24 hours reperfusion. At the end of study, the heart was harvested for area at risk and infarct size determination. A representative photograph of 5 TTC stained cardiac sections of a heart is shown in FIG. 3. The myocardial infarct stained white (TTC negative), while the ischemic region stained red, and non-ischemic region stained dark blue. Also shown is a manually segmented trace of the infarct area in the representative slice. The sum of the infarct size for all 5 slices was used to determine the overall area at risk and ischemic area as a percentage of left ventricle area at risk. The area at risk following the 30 minutes ischemia and 24 hours reperfusion insult was similar among the groups, indicating that animals were subjected to a similar ischemic insult (FIG. 4, Table 1). Myocardial infarct size is presented as % of left ventricle area at risk after a 30 minute ischemia and 24 hour reperfusion (FIG. 4, Table 1). At the low dose (1 mg/kg), albiglutide provided a marginal ~14% reduction (NS) in infarct size while the 3 and 10 mg/kg doses resulted in a 26% reduction (P<0.01) in infarct size normalized to area at risk when compared with vehicle following the 30 minute ischemia-24 hour reperfusion protocol. Recombinant human serum albumin (rHSA) was examined as an additional control for albiglutide. The dose used was 2.7 mg/kg (dose equivalent to 3 mg/kg albiglutide) and administered as outlined in FIG. 2. This equivalent dose of human serum albumin did not result in any observed cardioprotection (FIG. 5). Additionally, while heart rate was unaffected by albiglutide, left ventricle contractility (+dP/dt) was significantly increased with albiglutide at the 3 mg/kg dose, while +dP/dt, −dP/dt, and EDP were all improved at the 10 mg/kg dose (Table 1).

TABLE 1

Effect of albiglutide on infarct size and left ventricle hemodynamics. Data are n = 8-10 per group and presented as mean ± SEM.

|  | Vehicle | Albiglutide (1 mg/kg) | Albiglutide (3 mg/kg) | Albiglutide (10 mg/kg) |
| --- | --- | --- | --- | --- |
| Infarc size (% of ischemic area) | 53.3 ± 2.0 | 45.7 ± 2.4 | 39.4 ± 3.7** | 39.5 ± 2.1** |
| Ischemic area (% of left ventricle) | 39.7 ± 2.5 | 41.4 ± 2.7 | 42.9 ± 2.2 | 39.6 ± 1.6 |
| Heart rate (bpm) | 408 ± 14 | 386 ± 9 | 412 ± 8 | 409 ± 12 |
| LVSP (mmHg) | 94 ± 3 | 94 ± 4 | 99 ± 2 | 102 ± 3 |
| LVEDP (mmHg) | 11 ± 1 | 10 ± 1 | 10 ± 1 | 8 ± 1** |
| $dP/dt_{max}$ (mmHg/s) | 5921 ± 194 | 6112 ± 434 | 7033 ± 257** | 7461 ± 475* |
| $dP/dt_{min}$ (mmHg/s) | 4924 ± 297 | 4978 ± 395 | 5436 ± 224 | 6254 ± 537 |

*p < 0.05 vs vehicle;

**p < 0.01 vs vehicle by t-Test.

Data are mean ± SEM, n = 8-10/group.

t-Test

*p < 0.05 vs. vehicle;

**p < 0.01 vs. vehicle

Clinical chemistry measurements of plasma glucose, lactate, and insulin were measured at both pre-ischemia (at time of ischemic surgery) and 24 hours post-reperfusion (end of study). Albiglutide resulted in a reduction in plasma glucose and increase in insulin at all doses, albeit not dose related, when measured prior to the ischemic insult (Table 2). Lactate was also increased at the 3 and 10 mg/kg dose. However, following 24 hours of reperfusion, the effects of albiglutide on glucose and insulin were lost while lactate levels were still increased (Table 2).

Metabolic Gene Transcription

Taqman RT-PCR analysis was performed using a refined panel of 24 genes involved in regulation of glucose and fat metabolism with both naïve and I/R heart tissues following 3 days of treatment with albiglutide at 10 mg/kg. ACSL1, CPT1B, GAPDH, IGF1R, SLC2A4, HK2, GYS1, ESSRA, HIF1A, PPARGC1A, PDHA1, ALDOC, GSK3B, AKT1 increased significantly in naïve hearts following treatment with albiglutide (Table 3). Although fewer genes (GYS1, SLC2A4) were upregulated significantly in the ischemic

TABLE 2

Effect of albiglutide on body weight, clinical chemistry, and terminal pk.
Data are n = 8-10 per group and presented as mean ± SEM.

|  | Vehicle | albiglutide (1 mg/kg) | albiglutide (3 mg/kg) | albiglutide (10 mg/kg) |
| --- | --- | --- | --- | --- |
| Body weight (g) | 279 ± 6 | 278 ± 4 | 293 ± 7 | 290 ± 8 |
| Body weight change (g/day) | 7 ± 1 | 8 ± 1 | 5 ± 1 | (—)5 ± 3** |
| Insulin (pre -ischemia, pg/ml) | 446 ± 160 | 2546 ± 500** | 1744 ± 491* | 1987 ± 418** |
| Insulin (post -ischemia, pg/ml) | 577 ± 91 | 1506 ± 568 | 629 ± 169 | 553 ± 109 |
| Glucose (pre -ischemia, mg/dL) | 214 ± 5 | 166 ± 4** | 170 ± 7** | 157 ± 7** |
| Glucose (post -ischemia, mg/dL) | 197 ± 12 | 229 ± 13 | 216 ± 9 | 196 ± 18 |
| Lactate (pre -ischemia, mg/dL) | 13 ± 1 | 14 ± 1.7 | 17 ± 1.4* | 21 ± 2.1** |
| Lactate (post -ischemia, mg/dL) | 11 ± 1.2 | 16 ± 2* | 14 ± 1.2 | 16 ± 1.6** |
| Terminal PK (post -ischemia, ng/ml) | NA | 574 ± 125 | 1238 ± 133 | 8636 ± 1375 |

*p < 0.05 vs vehicle;

**p < 0.01 vs vehicle by t-Test.

Data are mean ± SE, n = 8-10/group.

t-Test;

*p < 0.05 vs. vehicle;

**p < 0.01 vs. vehicle

Following 2 days of albiglutide dosing, rats had a dose linear response in terms of reduced food consumption and weight gain compared with the vehicle group (Table 2, FIG. 6). The final plasma concentration of albiglutide at end of study was 574 ng/ml, 1238 ng/ml, and 8636 ng/ml for the 1 mg/kg, 3 mg/kg, and 10 mg/kg doses respectively (Table 2).

cAMP levels in the ischemic and non-ischemic regions of the heart were measured in a separate group of animals. While cAMP concentrations were not elevated following albiglutide treatment (10 mg/kg) in the non-ischemic LV, cAMP levels were normalized in the ischemic region.

region of the I/R hearts, several genes associated with glycolysis and glycogenesis (ALDOC, CPT1B, IGF1R, PDHA1, GSK3B, GYS1, SLC2A1) increased significantly in the non-ischemic region of the I/R hearts following treatment with albiglutide. Principle Component Analysis (PCA) of the gene expression data collected from all three heart tissue samples suggests clustering of both normal and non-ischemic data following treatment with albiglutide, which is consistent with a definite alteration in regulation of glucose and fat metabolism genes in both naïve and non-ischemic regions of the heart.

TABLE 3

Effect of albiglutide on metabolic gene transcriptional changes in the heart

| GENE | Gene Name | Albiglutide vs. Vehicle (Fold Change) | p Value |
|---|---|---|---|
| ACSL1 | Acetyl CoA Synthase 1 | 1.42 | *** |
| CPT1B | Carnitine Palmitoyltransferase 1B (muscle) | 1.44 | *** |
| GAPDH | Glyceraldehyde 3-Phosphate Dehydrogenase | 1.24 | *** |
| IGF1R | Insulin Growth Factor 1R | 1.36 | *** |
| SLC2A4 | Glucose Transporter 4 | 1.34 | *** |
| HK2 | Hexokinase 2 | 1.41 | *** |
| GYS1 | Glycogen Synthase | 1.21 | ** |
| ESSRA | Estrogen Receptor, alpha isoform | 1.29 | ** |
| HIF1A | HIF-1 a | 1.22 | ** |
| PPARGC1A | PGC1a | 1.28 | ** |
| PDHA1 | Pyruvate Dehydrogenase | 1.17 | * |
| ALDOC | Fructose 1,6 Bisphophate Aldolase | 1.36 | * |
| GSK3B | Glycogen Synthase Kinase | 1.16 | * |
| AKT1 | AKT1 | 1.13 | * |
| SLC2A1 | Glucose Transporter 1 | 1.24 | NS |
| PYGL | Glycogen Phosphorylase | −1.33 | NS |
| PRKAA2 | AMPK | 1.06 | NS |
| PPARG | PPAR Gamma | 1.12 | NS |
| HK1 | Hexokinase 1 | 1.06 | NS |
| PDK1 | Pyruvate Dehydrogenase Kinase | 1.28 | NS |
| UCP2 | Uncoupling Protein 2 | 1.16 | NS |
| ACTB | B- Actin | 1.03 | NS |
| LDHA | Lactate Dehydrogenase-1 (LDH-1) | 1.02 | NS |
| UCP3 | Uncoupling Protein 3 | −1.04 | NS |

Gene transcription regulation in albiglutide vs vehicle treated hearts.
Data are presented as fold change vs. vehicle.
* $p < 0.5$,
** $p < 0.01$,
*** $p < 0.001$,
NS, not significant.

Cardiac Energetics

Cardiac MRI was used to assess LV function at 24 h post-I/R injury. Although the vehicle-treated rats had significantly reduced LV ejection fractions and increased LV end systolic volumes compared to sham, albiglutide treatment prevented the deleterious cardiac remodeling and function decline (FIG. 7A, B). $^{31}$P MRS spectroscopy was performed to measure high energy phosphate peaks (PCr, ATP, Pi) in the heart. The PCr/ATP ratio was variable and while it appeared to be lower in the vehicle group, the trend was not significant (FIG. 7C). However, whereas the PCr/P, ratio and the cellular pH were decreased in the vehicle group vs. sham (p<0.05), albiglutide prevented a change in these parameters (FIG. 7D, E, respectively). Additionally, absolute whole heart ATP and PCr concentrations were markedly lower in vehicle-treated hearts compared to sham and albiglutide-treated hearts. (FIG. 7F, G).

Discussion

Albiglutide significantly reduced myocardial infarct size in dose-dependent manner following myocardial ischemia-reperfusion injury. Albiglutide also improved post-ischemic left ventricular cardiac function. While the exact mechanism by which albiglutide rendered the cardioprotection observed was not addressed in this study, this protection may, at least in part, be associated with increased insulin secretion and regulation of glucose metabolism following ischemia. The reduction in body weight observed with albiglutide was consistent with the reduction in food intake and expected pharmacology of GLP-1 agonists on increasing satiety. These data suggest not only that albiglutide will be safe in patients with coronary artery disease, but also that albiglutide may have beneficial effects in patients with acute MI or chronic heart failure.

Example 2

Albiglutide Increases Cardiac Glucose Uptake and Metabolism in an Insulin Independent Manner Methods
In Vivo 2-Deoxyglucose Experiment
Male Sprague-Dawley rats (~250-350 g body weight) that were purchased from Charles River with indwelling carotid and jugular catheters were used for the study. The following study groups were included in the study:
Group 1: vehicle; n=15
Group 2: albiglutide (10 mg/kg); n=16
Ex vivo Langendorff perfused heart experiment
Male Sprague-Dawley rats (~250-300 g body weight) that were purchased from Charles River were used for the study. The following study groups were included in the study:
Group 1: vehicle; n=13
Group 2: albiglutide (10 mg/kg); n=13
Experimental Protocol(s)
In Vivo 2-Deoxyglucose Experiment
Purpose: to estimate the amount of glucose uptake by cardiac tissue using tracer amount (10 µci/100 g body weight) of [3h]-2-deoxyglucose.
Animal Protocol:
1. Rats that were purchased from Charles Rivers with jugular and carotid cannulae in place. Rats were administered with Vehicle or albiglutide, 10 mg/kg at 1 ml/kg volume by subcutaneous injection at 48 h, 24 h and 2 h prior to the 2-Deoxyglucose (2-DG) experiment. Rats were fasted overnight prior to initiation of the 2-DG administration (FIG. 8).
2. 2-[$^3$H]DG, (~30 µCi, 100 µCi/kg body weight) was injected as a bolus into the jugular vein via a jugular catheter.

3. Blood (~200 μl) was sampled from the same catheter immediately before and at 5, and 20 minutes after tracer injection.
4. The final blood (1 ml) was drawn at 30 minutes post tracer injection.
5. Blood was collected in syringes containing anticoagulant and transferred to micro centrifuge tubes and centrifuged to separate plasma. Samples were saved in a –80 degree freezer
6. After study completion, the whole heart was rapidly dissected out and snap frozen in liquidnitrogen.
7. Radioactivity in these samples was assessed at a later date.

Tissue Extraction Protocol:

Determination of plasma glucose concentration: Plasma (60 μl) was diluted with water (540 μl), deproteinized by adding 300 μl each of 0.3 N Ba(OH)$_2$ and 0.3 N ZnSO$_4$, and centrifuged at 10,000 g (at 4° C. for 10 min).

Determination of plasma 2-[$^3$H]DG and tissue 2-[$^3$H]DG-6-P: The $^3$H content in deproteinized plasma (200 μl) was determined by scintillation counting in 1 ml of Optiphase supermix and 200 μl of this radioactive mix was counted on a Micorbeta unit. The raw counts were reported.

Portions of tissues (200-300 mg) were weighed and homogenized in 500 μl ice-cold 0.5 M perchloric acid using 6 mm ceramic beads on a tissue lyzer. Homogenates were centrifuged (10 min at 10,000), and resultant supernatants were neutralized (pH ~7.4) with 5 M KOH plus 0.5 M triethanolamine hydrochloride with the help of pH paper and centrifuged (10 min at 10,000 g). Most of the procedures were performed at room temperature unlike suggested in the paper. A portion (200 μl) of the neutralized extract was reconstituted in 1 ml of Optiphase supermix and 200 μl of this radioactive mix was counted on a Microbeta unit to access total radioactivity (2-[$^3$H]DG+2-[$^3$H]DG-6-P). Another aliquot (200 μl) was mixed with 200 μl of 0.3 N Ba(OH)$_2$ and 0.3 N ZnSO$_4$. This mixture was centrifuged, and the supernatant was used to determine unphosphorylated 2-[$^3$H]DG levels by using a portion (200 μl) of the neutralized extract was reconstituted in 1 ml of Optiphase supermix and 200 μl of this radioactive mix was counted on a Microbeta unit. Quench corrections were not made at this time. Tissue 2-[$^3$H]DG-6-P was calculated as the difference between total and 2-[$^3$H]DG values.

Adjusting the pH of the extract: Most extracts were neutralized with 40 μl (4 drops, 200 μl pipette tip) of 5 N KOH and 200 μl (+50 or 100 μl) of 0.5N Triethanolamine hydrochloride.

Determination of glucose disposal flux: Determination of the glucose disposal flux was based on the following equation and its principal components (i.e. average plasma glucose concentration (PGC$_{average}$), heart tissue radioactivity (HR$_{end}$), and plasma glucose radioactivity AUC (PR$_{total\_glucose}$ area under the curve):

Glucose uptake in heart $$\text{Flux} = \frac{PGC_{average} \times HR_{end}}{\int_{t=5}^{t=30} PR_{total\_glucose} \, dt}$$

Ex Vivo Langendorff Perfused Heart Experiment

Purpose: The purpose of this study is to determine whether albiglutide can promote glucose metabolism directly in the heart.

Cardiac Glucose Uptake Measurement In Vivo

In order to examine the role of albiglutide on cardiac glucose disposal in vivo, rats were administered vehicle or albiglutide (10 mg/kg/day for 3 days) as described above (n=14-15 per group). The rats then received an intravenous injection of 2-[$^3$H] deoxyglucose (2-[$^3$H] DG). Plasma samples were collected every 5 min up to 30 min to determine the plasma clearance of radioactivity. The hearts were freeze clamped and extracted with perchloric acid. Deproteinized plasma (200 μl) was added to 1 ml of Optiphase supermix and the $^3$H content was determined by scintillation counting using a Microbeta Trilux Unit (PerkinElmer, Model 1450-02). Raw counts are reported. Tissue 2-[$^3$H] DG-6-P was calculated as the difference between total radioactivity and 2-[$^3$H] DG values. Glucose disposal flux was determined using the average plasma glucose concentration, terminal heart tissue radioactivity, and plasma glucose radioactivity AUC (area under the curve) as previously described (Kraegen, et al. Am J Physiol 1985 March; 248(3 Pt 1):E353-E362).

Direct Cardiac Glucose Uptake Measurement in Langendorff Perfused Hearts

In order to examine the direct role of albiglutide on cardiac glucose disposal, rats were administered vehicle or albiglutide (10 mg/kg/day for 3 days) as described above (n=13 per group) prior to ex vivo measurement in perfused heart. The Langendorff perfused heart preparation was previously described (Willette, et al., *J Pharmacol Exp Ther* 2008 August; 326(2):443-52). After a stabilization period (15 min), baseline solution was collected to determine the baseline glucose and lactate concentrations prior to perfusing the heart with recirculation solution (~60 ml) containing vehicle or albiglutide (0.12 μM) under a constant pressure (75 mmHg). At the end of the perfusion period (30 min), perfusion solution was collected to measure the volume and glucose and lactate concentrations. Glucose and lactate were measured using an Olympus AU 640 analyzer (Olympus America Inc., Melville, N.Y.). The glucose flux was determined as (concentration of glucose (initial)-concentration (final))×(perfusion volume/heart wet weight (g)/time (h)); Lactate flux was determined as (concentration of lactate (final)-concentration (initial))×(perfusion volume/heart wet weight (g)/time (h)).

Cardiac Metabolic Flux Assessment

Two separate experiments were performed to examine cardiac intermediary metabolism: 1) relative carbohydrate vs. free fatty acid oxidation was assessed following an in vivo glucose clamp experiment, and 2) lactate flux and oxidation were assessed in the Langendorff perfused heart. In both experiments, rats were treated with vehicle or albiglutide (10 mg/kg/day for 3 days) as described above.

For the glucose clamp experiment, rats (n=5 per group) were subjected to a euinsulinemic-hyperglycemic clamp (continuous [1-$^{13}$C] glucose (8 mg/kg/min)/somatostatin (1.5 μg/min) infusion via jugular vein) lasting for 120 min. This period was sufficient for glycolytic and tricarboxylic cycle intermediates to achieve steady-state enrichments. At the end of the clamp experiment, the heart was rapidly removed and placed in liquid N$_2$. Perchloric acid extracts were prepared from frozen heart tissue, neutralized with KOH, lyophilized, and subsequently dissolved in 500 μl D$_2$O. The POCE (Proton Observe Carbon Enhanced) $^1$H MRS measurements of metabolite $^{13}$C enrichments in tissue extracts were performed at 9.4T spectrometer as previously reported (Yue, et al., *J Pharmacol Exp Ther* 2008 May; 325(2):466-74; Jucker, et al. *Am J Physiol* 1997 July; 273 (1 Pt 1):E139-E148; Jucker, et al. *J Biol Chem* 1997 April 18; 272(16):10464-73; and Yue, et al. *Circulation* 2003 Nov. 11; 108(19):2393-9). Relative cardiac carbohydrate (including glucose, glycogen, pyruvate, and lactate) and free fatty acid (FFA)/ketone oxidation in terms of relative substrate contribution to acetyl-CoA oxidation was assessed from the metabolite pool enrichments as follows: the relative carbohydrate oxidation rate was calculated as: ($4$-$^{13}$C glutamate enrichment)/($3$-$^{13}$C alanine enrichment), and the relative fat oxidation is calculated as: $1$-($4$-$^{13}$C glutamate enrichment)/($3$-$^{13}$C alanine enrichment).

For assessing lactate oxidation and flux, a perfused heart experiment was performed in which $3$-$^{13}$C lactate was used as a precursor for lactate oxidation measurements. Following the dosing paradigm, rats (n=10 per group) were anesthetized with Nembutal (60 mg/kg, ip) and heparinized with sodium heparin (200 U/kg, ip). The heart was rapidly excised and transferred into ice-cold buffered Krebs-Henseleit (KH) solution, consisting of 118.5 mM NaCl, 4.7 mM KCl, 1.2 mM $CaCl_2$, 1.2 mM $MgSO_4$, 25 mM $NaHCO_3$, 1.2 mM $KH_2PO_4$, 11 mM glucose, pH 7.4. The aorta was cannulated using a steel aortic cannula prior to connecting to the Langendorff apparatus [Isolated Heart Size 1 (1H-1); Harvard Apparatus Inc., Holliston, Mass.] and perfused at a constant pressure of 70 mm Hg with KH solution (37° C.) gassed with 95% $O_2$, 5% $CO_2$ via a glass frit. After a period of stabilization, albiglutide (120 nM) or vehicle was added to a modified KH solution consisting of 118.5 mM NaCl, 4.7 mM KCl, 1.2 mM $CaCl_2$, 1.2 mM $MgSO_4$, 25 mM $NaHCO_3$, 1.2 mM $KH_2PO_4$, 11 mM glucose, 3% BSA (essentially fatty acid free), 1 mM $3$-$^{13}$C sodium lactate, 0.1 mM sodium pyruvate and 0.4 sodium palmitate, pH 7.4. The heart was perfused for 60 minutes during which influent and effluent samples were collected and lactate concentration was analyzed using an Olympus AU640 analyzer. In addition influent and effluent $3$-$^{13}$C lactate enrichments and heart tissue $3$-$^{13}$C lactate, $3$-$^{13}$C alanine, and $4$-$^{13}$C glutamate enrichments were measured by NMR spectroscopy and relative lactate oxidation as substrate contribution to acetyl-CoA was calculated as: ($4$-$^{13}$C glutamate enrichment)/($3$-$^{13}$C alanine enrichment).

Animal Protocol: Rats were administered vehicle or albiglutide, 10 mg/kg, with a dose volume of 1 ml/kg by subcutaneous injection at 48 h, 24 h and 2 h before harvesting the heart and subjecting to perfusion with recirculating buffered solution (FIG. 11). Albiglutide (0.12 uM) was added to perfusion solution according to the expected plasma concentration of albiglutide at the time of cardiac harvest. Rats were anesthetized with Nembutal (60 mg/kg, ip) and heparinized with sodium heparin (200 U/kg, ip). The heart was rapidly excised and transferred into ice-cold buffered Krebs-Henseleit (KH) solution, consisting of 118.5 mM NaCl, 4.7 mM KCl, 1.2 mM $CaCl_2$, 1.2 mM $MgSO_4$, 25 mM $NaHCO_3$, 1.2 mM $KH_2PO_4$, and 11 mM glucose, pH 7.4. The aorta was cannulated using a steel aortic cannula. After the aorta was cannulated, the heart was connected to the Langendorff apparatus [Isolated Heart Size 1 (1H-1); Harvard Apparatus Inc., Holliston, Mass.] and perfused at a constant pressure of 75 mm Hg with KH solution (37° C.) gassed with 95% $O_2$, 5% $CO_2$ via a glass frit. After stabilization period, baseline buffer solution was collected to determine the baseline glucose and lactate concentration, then the heart was perfused with recirculation buffered solution (~60 ml) for 1 h under a constant pressure (75 mmHg). At the end of the perfusion, perfusion buffered solution was collected to measure the volume and glucose and lactate concentrations. Heart wet weight was determined as well. Glucose and lactate were measured by the clinical chemistry lab using Olympus AU 640 analyzer. Glucose flux was determined as (concentration of glucose (initial)−concentration (end))×(perfusion volume/heart wet weight (g)/time (hr)); Lactate was determined as (concentration of glucose (end)−concentration (initial))×(perfusion volume/heart wet weight (g)/time (hr)).

Diet: Normal rodent diet

Analytical Measurements: Insulin was measured using an MDS rat insulin kit. Blood glucose and lactate were determined using an Olympus AU640 clinical chemistry analyzer. Plasma glucose was measured using a glucose assay kit (192 well: Cat No: 10009582, Lot No: 0414573). During the in vivo experiment blood glucose was measured using ACCU CHECK Advantage (Cat/Type: 3288650): Accu-check comfort curve (100 test strips, Roche, Lot No: 551017).

Drugs and Materials

The following drug material was used in the study:
1) Albiglutide
2) Vehicle (10 mM Sodium Phosphate, 153 mM Mannitol, 117 mM Trehalose, 0.01% (w/v) Polysorbate 80, pH 7.2.

Preparation Vehicle/Drug/Reagents:

Approximately 900 mL of HPLC grade water was added to a beaker. A clean stir bar was added and the following were mixed on a magnetic stir plate: 0.41±0.01 g of sodium phosphate monobasic monohydrate, 0.99±0.01 g sodium phosphate dibasic anhydrous, 44.26±0.1 g D-trehalose dehydrate, 27.87±0.1 g mannitol, and 10 mL of a 1% Polysorbate 80 stock solution. pH was measured and, if necessary, the pH was adjusted to 7.2 using 1N sodium hydroxide or phosphoric acid. The solution was transferred to a 1000 mL volumetric flask and HPLC grade water was added until the final volume of 1000 mL was reached before stirring for at least 20 minutes. The buffer was filtered through a 0.2 micron filter unit assembly. The flask was stored at 4° C. protected from light by wrapping the flask in aluminium foil. Stock solution (131 mg/ml) stored in −80° C. freezer was diluted with vehicle to the working solution of 10 mg/ml albiglutide.

Data Analysis

Data are presented as mean±SEM. Differences between groups were compared by paired and unpaired Student's t tests. P<0.05 was considered statistically significant. A Grubb's outlier test was used for the principal components of the in vivo 2-DG uptake experiment (i.e. average glucose concentration, heart tissue radioactivity, and AUC plasma radioactivity). It was determined that there was a clear outlier when (z(outlier)>z_critical(2.6)).

Results

Body weight was significantly reduced in the treated group (FIG. 9). The vehicle group also showed some weight loss as a result of the overnight fast prior to the experiment.

All principle components of the in vivo 2-DG experiment including average plasma glucose, heart tissue radioactivity, and plasma glucose radioactivity (AUC) were carefully examined for statistical outliers in the study in order to minimize the observed variability in the heart glucose uptake measurement. When examining the principal components of the glucose flux measurement for outliers using the Grubb's test, it was determined that there was a clear outlier (z(3.2)>z_critical(2.6)) in the heart tissue radioactivity with one of the vehicle animals. Additionally, the average plasma glucose of one of the albiglutide treated animals was found to be high (z(2.7)>z_critical(2.6)). The 2-DG uptake in the heart increased significantly (70%, P=0.022) following treatment with albiglutide (N=15) compared to vehicle treatment (N=14) with the exclusion of one vehicle animal and one albiglutide treated animal (FIG. 10).

There were no significant differences between groups with respect to plasma glucose, lactate, non-esterified fatty acids, or insulin following 2 days of albiglutide dosing.

Ex vivo glucose disposal (glucose uptake and lactate efflux) was evaluated in the Langendorff perfused heart setup using the same in vivo dosing protocol as was used for the in vivo 2-DG study followed by a continuous perfusion of albiglutide at 120 nM (the plasma concentration achieved at the end of the in vivo study) (FIG. 10). A schematic of the recirculating bath in the Langendorff retrograde perfusion prep is shown in FIG. 12. As was the case with the in vivo 2-DG experiment, the rats treated with albiglutide lost weight during the dosing paradigm. The glucose disposal was increased by 59% (P<0.05) in the albiglutide treated hearts (FIG. 13) while lactate efflux was decreased in albiglutide treated hearts compared to vehicle treated hearts (↓55%, P<0.05) (FIG. 13).

Cardiac Glucose Intermediary Metabolism

To determine the effect of albiglutide on cardiac intermediate glucose metabolism, metabolic substrate utilization was assessed using a 1-$^{13}$C glucose euinsulinemic-hyperglycemic clamp. There were no differences in alanine and lactate enrichments between vehicle- and albiglutide-treated hearts (FIG. 14A). However, enrichment of 4-$^{13}$C glutamate, a TCA cycle intermediate, was significantly higher in the albiglutide-treated heart compared to vehicle-treated heart reflecting increased glycolytic flux into the TCA cycle (FIG. 14A). Furthermore, treatment with albiglutide resulted in a significantly increased relative ratio of carbohydrate versus fat oxidation (↑112%, p<0.05 vs. vehicle) as calculated by isotopomer analysis of alanine and glutamate enrichments (FIG. 14B). Cardiac glycogen levels were similar in both albiglutide and vehicle treated hearts (12.2±1.7 vs. 11.4±3.5 µmol/g respectively). However, albiglutide did not alter the metabolic profile in the ischemic heart.

To further explore the effect of albiglutide treatment on cardiac lactate metabolism, 3-$^{13}$C lactate cardiac flux and oxidation were assessed in the Langendorff perfused heart under physiological conditions of substrate availability (i.e. inclusion of glucose, lactate, pyruvate, FFA at physiological levels). Albiglutide transiently increased lactate influx into the perfused heart over 30 min (FIG. 15A) (negative efflux) while having no effect on cardiac lactate concentration in this experiment (FIG. 15B). Yet, albiglutide treatment resulted in an increased relative lactate oxidation compared to vehicle (↑63%, p<0.05, FIG. 15C) as assessed by isotopomer analysis consistent with previous in vivo findings using labeled glucose as the precursor.

Discussion

Albiglutide significantly increased cardiac glucose uptake in the normal heart and was confirmed using two different measuring methods (i.e. in vivo 2-deoxyglucose uptake and ex vivo Langendorff perfused heart). The data suggest that this increase in glucose uptake by the heart is mediated via an insulin independent mechanism as has been shown before with GLP-1 infusion (Ban, et al. *Circulation*. 2008; 117: 2340) (Zhao, et al. *J Pharmacol Exp Ther*. 2006; 317(3): 1106). In addition, either non-oxidative (e.g. glycogen synthesis) or oxidative (aerobic glycolysis) glucose disposal was stimulated in the normal heart with albiglutide as reflected by the decrease in lactate efflux in the perfused heart setup. The reduction in body weight observed with albiglutide was consistent with the reduction in food intake and expected pharmacology of GLP-1 agonists on increasing satiety. These data suggest that the cardioprotection observed in albiglutide treated rats undergoing ischemia-reperfusion injury, may in part be explained by the increase in glucose disposal and metabolism by the heart.

Example 3

A Multi-Center, Placebo-Controlled, Study to Evaluate the Safety of Albiglutide and its Effects on Myocardial Metabolism, Myocardial Function, and Exercise Capacity in Patients with Non-Ischemic Cardiomyopathy and NYHA Class II/III Congestive Heart Failure In the normal human myocardium, the majority (60-90%) of energy for cardiac function is derived from fatty acid oxidation (FAO), with the remainder (10-40%) being derived from glucose oxidation (GO). The normal heart is capable of dynamically modulating rates of myocardial FAO and GO in response to substrate availability, which in turn allows the heart to store energy in the form of high energy phosphates, specifically ATP and phosphocreatine. This ensures that the heart maintains adequate energy reserves both to maintain basal function and to augment contractility in response to increased demand. However, in patients with dilated cardiomyopathy only about 20% of energy is supplied by FAO, with the remainder being supplied by GO (Davila-Roman V G, et al. JACC 2002). This metabolic substrate shift toward a preference for glucose may in part be a consequence of glucose being energetically more efficient (lower oxygen usage) than fat. However, despite a relatively higher dependency on glucose, there is evidence that both glucose uptake and utilization are impaired, and that myocardial insulin resistance persists in these patients. This reduction in the capacity to metabolize fatty acids and glucose is associated with reduced myocardial ATP content and reduced overall high energy phosphate availability, and this impaired energetic state likely contributes to the impaired myocardial function that characterizes the disease. Together, these observations suggest the hypothesis that in patients with dilated cardiomyopathy and CHF, activation of myocardial glucose metabolism or an increase in the availability of glucose to the myocardium may result in improved myocardial energetics and improved cardiac function. Thus, therapies such as GLP-1 agonists could increase myocardial insulin action resulting in improved glucose oxidation and ultimately improved ventricular efficiency and exercise capacity.

Glucogan-like peptide-1 (GLP-1) is an incretin hormone secreted by intestinal L-cells in response to nutrient ingestion. GLP-1 regulates glucose homeostasis by stimulating insulin secretion, inhibiting glucagon secretion, delaying gastric emptying and promoting satiety. Although the major physiological function of GLP-1 is associated with glycemic control, increasing evidence indicates that GLP-1 may also play an important role in cardiovascular physiology. GLP-1 receptors are also expressed in cardiovascular tissues and activation of GLP-1 receptors by agonists results in a wide range of cardiovascular effects (Grieve, et al.). GLP-1 has been shown to function as an insulinomimetic in the heart as it can directly modulate glucose metabolism in the heart (Ban, et al. *Circulation*. 2008; 117:2340). It has been demonstrated that GLP-1 protects the heart against myocardial ischemia-reperfusion injury both ex vivo (Ban, et al. *Circulation*. 2008; 117:2340) and in vivo (Bose, et al. *Circulation*. 2008; 117:2340). Most importantly, it has been reported that short-term infusion of GLP-1 for 72 h significantly improves cardiac function in heart failure patients, suggesting GLP-1 and mimetics may be used as a novel therapeutic approach for heart failure (Nikolaidis, et al. *Circulation*. 2004; 109:962-5).

In this study we will use FDG-PET to measure myocardial glucose uptake as a measure of myocardial insulin action and a surrogate for glucose oxidation. Glucose uptake will then be correlated with changes in left ventricular efficiency and exercise capacity.

An increasing body of evidence indicates that end-stage heart failure is characterized by impaired capacity to metabolize fatty acids and glucose, the two main metabolic substrates of the heart. The resulting myocardial energy depletion in the form of reduced myocardial ATP and phosphocreatine content is thought to be an important contributor to impaired ventricular function and reduced cardiac output. Specifically, myocardial insulin resistance is believed to play an important role in the pathogenesis of heart failure that is associated with diabetes.

Studies in multiple animal models of acute myocardial injury and chronic heart failure have demonstrated that administration of GLP-1 receptor agonists results in reduced myocardial injury and improved myocardial function (Timmers L, et al., *J Am Coll Cardiol* 2009; 53:501; Noyan-Ashraf M., et al., *Diabetes* 2009; 58:975; Ban K, et al., *Circulation* 2008; 117:2340; Nikolaidis L, *Circulation* 2004; 110:955). As shown in Example 1 herein, albiglutide significantly reduces infarct size in an acute myocardial ischemia/reperfusion injury model in the rat. Also shown in Examples 1 and 2, herein, the significant reduction in infarct size was dose-dependent. Post-ischemic left ventricular cardiac function also improved. The exact mechanism by which albiglutide afforded cardioprotection in the rodent model was not explored; however, an indirect effect of increased insulin secretion, or a direct effect of GLP-1 receptor agonism on the myocardium, can be postulated. In ongoing experiments to examine myocardial glucose uptake, preliminary data indicate the ability of both GLP-1 peptide and albiglutide, to increase glucose uptake in vivo and in vitro.

The effects of GLP-1 receptor agonism on myocardial function have been explored in several pilot clinical studies using continuous infusion of GLP-1 peptide. These studies have reported that GLP-1 peptide infusion increases exercise capacity in subjects with chronic heart failure (Sokos G, et al., *J Cardiac Failure* 2006; 12:684), improves left ventricular ejection fraction in patients with acute myocardial infarction (Nikolaidis L, et al., *Circulation* 2004; 109:962), and reduces the need for administration of intravenous pressor agents in patients following cardiac surgery (Sokos G, et al., *Am J Cardiol* 2007; 100:824). The major mechanism by which GLP-1 administration produces beneficial effects on cardiac function in each case is thought to be through amelioration of myocardial insulin resistance and improved myocardial glucose utilization. Based on the existing preclinical data, and the clinical evidence with GLP-1 peptide that supports a beneficial effect of GLP-1 agonists on myocardial function, we hypothesize that administration of albiglutide will promote myocardial glucose uptake and utilization/oxidation as well as increase myocardial insulin action in patients with chronic heart failure and impaired ventricular function, thereby improving overall cardiac energy efficiency and enhancing cardiac function.

This exploratory proof of concept study will be conducted in patients with stable New York Heart Association (NYHA) Class II-III heart failure with chronic non-ischemic dilated cardiomyopathy. The primary endpoints are directed at testing the hypothesis that Albiglutide administration will increase glucose uptake and utilization in the myocardium as measured by FDG-PET, resulting in increased myocardial efficiency and increased exercise capacity. A positive result defined as either statistically significant effects on one or more of the primary endpoints or as an overall signal suggesting a clinically relevant effect on myocardial physiology would provide evidence for potential progression into further development in a chronic heart failure population.

Dose Rationale

This Phase II proof-of-concept study will evaluate the dose response, efficacy, safety, and tolerability of a range of doses of albiglutide compared to placebo over a 12-week treatment period in patients with NYHA class II/III heart failure. The planned doses to be given as once weekly subcutaneous injections are 3.75 mg, 15 mg, and 30 mg. The dose range was selected based on safety and tolerability data for albiglutide from previous studies, efficacy data for GLP-1 from published clinical studies evaluating its effects on cardiac function in patients with congestive heart failure, and pharmacodynamic data for albiglutide in preclinical experiments.

To establish a target concentration for efficacy, published data were reviewed from two studies that examined the effects of GLP-1 on cardiac function and clinical outcome in patients with chronic heart failure [Sokos, et al. *J Cardiac Failure;* 2006; 12:684] and in patients with acute myocardial infarction and left ventricular dysfunction after successful reperfusion [Nikolaidis, et al. *Circulation,* 2004; 109:962-965]. In these studies, GLP-1 plasma concentrations in the range of ~50-100 µM produced positive results. Sokos, et al. studied the use of GLP-1 in patients with NYHA class III/IV chronic heart failure (n=12) using a 5-week infusion of GLP-1 (2.5 µmol/kg/min) in addition to standard therapy. [Sokos, et al. *J Cardiac Failure;* 2006; 12:684]. Chronic GLP-1 treatment resulted in significant improvements in left ventricular ejection fraction (21±3% to 27±3%, p<0.01), maximum myocardial oxygen consumption (10.8±0.9 ml/O$_2$/min/kg to 13.9±0.6 mg/O$_2$/min/kg, p<0.001), 6 minute walk distance (232±15m to 286±12m, p<0.001) and Minnesota Living with Heart Failure quality of life score (64±4 to 44±5, p<0.01). A significant effect was not seen on any of these parameters in control patients (n=9). In the second study, GLP-1 administration (1.5 µmol/kg/min for 72 hours) resulted in a significant improvement in left ventricular ejection fraction in 10 patients with acute myocardial infarction after successful primary angioplasty (29±2% to 39±2%, p<0.01) as compared to a control group receiving standard therapy. Additionally, improvements in global wall motion score and regional wall motion score indices were observed (1.94±0.11 to 1.63±0.09, p<0.01 and 2.53±0.08 to 2.02±0.11, p<0.01, respectively) [Nikoladis, et al. *Circulation,* 2004; 109:962-965]. Again, these positive effects were not seen in the control group (n=11).

In vitro cell culture studies demonstrated that albiglutide is approximately 10-fold less potent as a GLP-1 receptor agonist than GLP-1. Using the upper limit of the GLP-1 range needed for efficacy, which was determined from the GLP-1 concentrations achieved in the published clinical studies, and taking into account the difference in potency and molecular weight, a target concentration of approximately 77 ng/mL of albiglutide was predicted to be required to produce a clinically important effect on left ventricular (LV) function. However, due to potential uncertainty around this estimate of the required target concentration, simulations were performed using a pharmacokinetic model developed from a previous study (16-week, dose ranging study comparing albiglutide to Byetta® in type II diabetic subjects) to evaluate if the dose range proposed for this study would meet the estimated target concentration given a wide range in potential potencies of albiglutide compared with that of native GLP-1. The target attainment rates for a range of possible doses and possible potency differences are presented in Table 4. Within the range of assumed potencies relative to native GLP-1, the proposed dosing range for this study has a high chance of attaining efficacious concentrations if the potency of albiglutide is between 10-100-fold lower than that of native GLP-1. If the potency of albiglutide for CHF is less than this, then the probability of reaching the target concentration is considerably lower and would likely require doses greater than 30 mg.

The current highest starting dose of 30 mg weekly was chosen because doses greater than 30 mg weekly were associated with significant GI adverse events. The frequency of nausea and/or vomiting was 29.0% when albiglutide was administered as 30 mg once weekly [Rosenstock, et al. *Diabetes Care* 2009; 32:1880-1886]. Comparatively, the frequency was 54.3% and 55.9% when it was administered as 50 mg biweekly or 100 mg monthly. It is possible to titrate to a dose higher than 30 mg if needed as the gastrointestinal (GI) events with the 50 mg dose declined with subsequent dosing.

The lowest dose was chosen as 3.75 mg in order to achieve a predicted 90% target attainment rate based on the in vitro potency data. Doses of 1.88 mg and 7.5 mg were not chosen for this study. The 1.88 mg dose does not achieve a predicted target attainment rate of 90% at a potency of 1/10 for albiglutide compared to native GLP-1. The 7.5 mg dose is predicted to provide little additional information compared to the 3.75 mg dose to aid in characterizing the dose-response curve.

TABLE 4

Target Attainment Rate for Average Plasma Concentration at Steady State ($Cp_{avess}$) Based on a Range of Assumed Potencies of Albiglutide Relative to GLP-1 Peptide.

| Target Average Concentration of Albiglutide at Steady State | Assumed Potency Relative to GLP-1 | Estimated Target Concentration Attainment Rate at Each Dose | | | | |
|---|---|---|---|---|---|---|
| | | 1.88 mg | 3.75 mg | 7.5 mg | 15 mg | 30 mg |
| 77 ng/mL | 1/10 | 86.2% | 99.8% | 100% | 100% | 100% |
| 770 ng/mL | 1/100 | 0% | 0.2% | 11.5% | 70.4% | 99.4% |
| 1930 ng/mL | 1/250 | 0% | 0% | 0% | 2.8% | 47.6% |
| 3870 ng/mL | 1/500 | 0% | 0% | 0% | 0% | 3.8% |

Objective(s)
Primary
  To determine the treatment effect across doses of albiglutide relative to placebo on myocardial glucose uptake in patients with NYHA Class II/III heart failure over a 3 month period.
  To determine the treatment effect across doses of albiglutide relative to placebo on myocardial efficiency in patients with NYHA Class II/III heart failure over a 3 month period.
  To determine the treatment effect across doses of albiglutide relative to placebo on exercise performance in patients with NYHA Class II/III heart failure over a 3 month period.
Secondary
  To determine the treatment effect across doses of albiglutide relative to placebo on left ventricular function using echocardiography.
  In a sub-study to be performed at a single site, to determine the treatment effect across doses of albiglutide relative to placebo on left and right ventricular volumes, ejection fraction and cardiac mass using cardiac magnetic resonance imaging (CMR).
  To determine the treatment effect across doses of albiglutide relative to placebo on 6-minute walking distance.
  To determine the treatment effect across doses of albiglutide relative to placebo on serum BNP, a marker of severity of CHF.
  To determine the treatment effect across doses of albiglutide relative to placebo on biomarkers of glucose metabolism.
  To determine the treatment effect across doses of albiglutide relative to placebo on quality of life measures
  To assess the safety and tolerability of albiglutide in patients with NYHA Class II/III heart failure over a 3 month treatment period.
  Exploratory pharmacokinetic/pharmacodynamic analyses may also be performed using trough plasma concentrations of albiglutide.
Endpoint(s)
Primary
  Myocardial glucose utilization as assessed by FDG-PET imaging
  Myocardial efficiency (work performed/$MVO_2$) assessed at rest:
    SV calculated by cardiac echo
    $MVO_2$ assessed via $^{11}$C-acetate PET imaging
  Peak oxygen uptake ($VO_2$ max) as assessed by bicycle cardiopulmonary exercise testing.
Secondary
  Left ventricular function (LVEF, LV volumes in systole and diastole) as assessed by echocardiogram at all centers.
  In a sub-study to be performed at a single site LV and RV function will also be assessed by cardiac magnetic resonance imaging (CMR) (LVEF, LV and RV volumes in systole and diastole, LV mass).
  Exercise capacity assessed by 6-minute walk test.
  Serum NT-BNP level.
  Plasma levels of glucose, insulin, free fatty acids; HOMA index.
  Quality of life as assessed by the Minnesota Living with Heart Failure Questionnaire.
  Exploratory PK parameters may be measured including (but not limited to) AUC, CMAX and Ct.
Safety Endpoints:
  Safety endpoints including but not limited to:
    a. incidence and severity of Aes
    b. all cause mortality
    c. hospitalization for heart failure
Investigational Plan
Study Design/Schematic
  This will be a multi-center, randomized, placebo controlled, single-blind (subjects and investigators will be blinded,), parallel-group design enrolling approximately 120 randomized subjects with stable NYHA Class II-III heart failure with chronic non-ischemic dilated cardiomyopathy.

Assuming a ~20% post-randomization drop-out rate for subjects randomized, this number will provide ~25 evaluable subjects in each arm [placebo, 3.75 mg, 15 mg and 30 mg albiglutide].

Subjects will be adaptively randomized into the study with stratification of gender by means of an interactive voice response system (IVRS) to receive one of the treatment regimens listed below.

A: albiglutide (3.75 mg)
B: albiglutide (15 mg)
C: albiglutide (30 mg)
D: albiglutide-matched placebo Subjects randomized to albiglutide or placebo will come into the clinic for weekly subcutaneously injections by site staff. Blood samples for safety, PK and PD analysis, as well as imaging, exercise testing, safety and tolerability assessments (including AEs, vital signs, ECGs, etc.) will be collected/assessed at study visits indicated in the Time and Events table. There will be two overnight stays during this study at Week 1 and Week 13 to allow for the imaging and exercise testing. The details of the overnight stays will be outlined in the Study Procedures Manuel (SPM). A follow-up visit will occur 28 days (±3 days) after the final dose of study medication.

If subjects discontinue prematurely, additional subjects may be enrolled at the discretion of the sponsor in consultation with the investigators. Based on ongoing safety, PK and PD data, additional subjects may be dosed at a given level if additional data are necessary to establish safety, tolerability or better characterize the PK and PD parameters or study additional dose levels.

The duration of participation in this study is expected to be approximately 20 weeks from screening to follow-up.

CMR Sub-Study

Eligible subjects enrolled at a single site also will undergo CMR scanning at baseline (week 1) before receiving an initial administration of albiglutide or albiglutide-matched placebo and in week 13 at the conclusion of the treatment period for the study.

Treatment Assignment

Subjects will be assigned to parallel treatment group sequences in accordance with the randomization schedule generated by Discovery Biometrics, prior to the start of the study, using validated internal software.

Subjects will be randomized into the study by means of an interactive voice response system (IVRS) to receive one of the treatment regimens listed below.

| Regimen | Description |
| --- | --- |
| A | 3.75 mg of albiglutide |
| B | 15 mg of albiglutide |
| C | 30 mg of albiglutide |
| D | albiglutide-matched placebo |

Dose Adjustment/Stopping Efficacy Criteria

Interim analyses are planned for this study in order to assess the effectiveness of the active dose levels and the utility of continued randomization into dose levels not achieving sufficient pharmacodynamic effects.

Eligibility Criteria for this Study Will Include:

A subject will be eligible for inclusion in this study only if all of the following criteria apply:

Chronic dilated cardiomyopathy of non-ischemic origin
Clinically stable on optimal therapies for at least 3 months prior to screening/baseline visit.
Left ventricular ejection fraction 35% as assessed by any measurement in the previous 12 months.
NYHA Class II/III heart failure for a minimum of 6 months prior to enrolment
Male or female between 21 and 75 years of age inclusive, at the time of signing the informed consent. However the optimal age range for this study will be 40 to 65 years of age.

A female subject is eligible to participate if she is of:
Non-childbearing potential defined as pre-menopausal females with a documented tubal ligation or hysterectomy; or postmenopausal defined as 12 months of spontaneous amenorrhea [in questionable cases a blood sample with simultaneous follicle stimulating hormone (FSH)>40 MIU/ml and estradiol <40 pg/ml (<140 pmol/L) is confirmatory]. [Females on hormone replacement therapy (HRT) and whose menopausal status is in doubt will be required to use one of the contraception methods if they wish to continue their HRT during the study. Otherwise, they must discontinue HRT to allow confirmation of post-menopausal status prior to study enrollment. For most forms of HRT, at least 2-4 weeks will elapse between the cessation of therapy and the blood draw; this interval depends on the type and dosage of HRT. Following confirmation of their post-menopausal status, they can resume use of HRT during the study without use of a contraceptive method.]

Child-bearing potential and agrees to use one of the contraception methods for an appropriate period of time (as determined by the product label or investigator) prior to the start of dosing to sufficiently minimize the risk of pregnancy at that point. Female subjects must agree to use contraception until the follow-up visit ~28 days post-last dose.

Capable of giving written informed consent, which includes compliance with the requirements and restrictions listed in the consent form.

Confirmed QTcB or QTcF <450 msec; or QTc <480 msec in subjects with Bundle Branch Block.

AST and ALT <2xULN; alkaline phosphatase and bilirubin 1.5xULN (isolated bilirubin >1.5xULN is acceptable if bilirubin is fractionated and direct bilirubin <35%).

Subjects must be able to perform performance/exercise testing

A subject will not be eligible for inclusion in this study if any of the following criteria apply:

A positive pre-study Hepatitis B surface antigen or positive Hepatitis C antibody result within 3 months of screening
History of drug/alcohol abuse.
A positive test for HIV antibody.
Calcitonin >100 pg./mL
Triglycerides >850 mg/dL
History of significant gastrointestinal surgery, including gastric bypass and banding, antrectomy, Roux-en-Y bypass, gastric vagotomy, small bowel resection, or surgeries thought to significantlyaffect upper gastrointestinal function.

History of regular alcohol consumption within 6 months of the study defined as:
For UK: an average weekly intake of >21 units for males or >14 units for females. One unit is equivalent to 8 g of alcohol: a half-pint (~240 ml) of beer, 1 glass (125 ml) of wine or 1 (25 ml) measure of spirits.
For US: an average weekly intake of >14 drinks for males or >7 drinks for females. One drink is equivalent to 12 g of alcohol: 12 ounces (360 ml) of beer, 5 ounces (150 ml) of wine or 1.5 ounces (45 ml) of 80 proof distilled spirits.

The subject has participated in a clinical trial and has received an investigational product within the following time period prior to the first dosing day in the current study: 30 days, 5 half-lives or twice the duration of the biological effect of the investigational product (whichever is longer).

Exposure to more than four new chemical entities within 12 months prior to the first dosing day.

Known allergy or history of sensitivity to albiglutide, any other GLP-1 analogue, or Baker's yeast.

Where participation in the study would result in donation of blood or blood products in excess of 500 mL within a 56 day period.

Pregnant females as determined by positive serum or urine hCG test at screening or prior to dosing.

Lactating females.

Unwillingness or inability to follow the procedures outlined in the protocol (e.g. related to psychiatric disorder)

Subject is mentally or legally incapacitated.

Known diagnosis of diabetes mellitus, fasting glucose >140 mg/dL, or HbA1c>7%.

Uncorrected thyroid disease manifest as an abnormal thyroid-stimulating hormone (TSH) (outside reference range at screening).

Other medical problems with life expectancy less than 1yr.

Other causes of cardiomyopathy or left ventricular dysfunction including:
  i. Uncorrected primary obstructive or regurgitant valvular disease
  ii. Restrictive cardiomyopathy due to amyloidosis, hemochromatosis, sarcoidosis or other cause
  iii. Cardiac hypertrophy with wall thickness >1.5 cm
  iv. Alcohol-induced cardiomyopathy
  v. Women with heart failure during the 12 months following childbirth.
  vi. Complex congenital heart disease
  vii. Anthracycline induced cardiomyopathy Subjects with genetic disorders of skeletal muscle (e.g. Duchenne muscular dystrophy)

Clinically significant pericardial disease.

Listed as a status 1A or 1B on heart transplant waiting list.

History of deep vein thrombosis or a known coagulation disorder

History of pancreatitis

History of or family history of medullary thyroid carcinoma

History of or family history of multiple endocrine neoplasia type 2

History of clinically significant CAD including any of the following:
  i. Prior STEMI leading to segmental wall motion abnormality
  ii. Presence of CAD with >70% obstruction of major vessel based on anatomy from prior coronary angiography
  iii. Hospitalization for unstable angina within past 6 months
  iv. High risk of having CAD in the judgment of the PI History of renal dysfunction with estimated GFR <60 ml/min at screening Resting systolic blood pressure <85 mmHg or >170 mmHg; or diastolic blood pressure >110 mgHg at screening.

Inability of the patient to lie flat for a combined total of up to 4 hours to complete imaging assessments.

No subjects will be enrolled at the single site performing the CMR sub-study who have contraindications to MRI scanning including, but not limited to:
  Intracranial aneurysm clips (except Sugita) with an appropriate operative conformation
  History of intra-orbital metal fragments
  Pacemakers or non-MR compatible heart valves
  Inner ear implants
  History of claustrophobia deemed significant by the investigator Myocardial Glucose Uptake

[$^{18}$F]fluoro-2-deoxy-glucose positron emission tomography (FDG-PET) imaging will be performed at baseline and end of treatment (week 13) to assess myocardial glucose uptake. Subjects will be admitted to the respective research unit or its component at each imaging site on the evening before each imaging/infusion study. At 1800 h, subjects will ingest a standard meal containing approximately 12 kcal/kg body wt. Carbohydrate, fat, and protein will represent approximately 55, 30, and 15%, respectively, of total energy intake. At 2000 h, subjects will ingest a defined liquid formula snack containing ~250 kcal, 40 g carbohydrate, 6.1 g fat, and 8.8 g protein. After this snack, all subjects will fast until completion of the study the following day. All studies will be initiated by ~0800 to minimize the effects of circadian rhythm on myocardial metabolism.

Myocardial Efficiency

One measure of myocardial efficiency if the work metabolic index (WMI) discussed in Lindner, et al. (J Nucl Med, 47, 378-3832005).

MVO$_2$ measurements using $^{11}$C-acetate: Myocardial oxygen consumption (MVO$_2$) will be estimated for each study by measuringthe rate of myocardial clearance of $^{11}$C-activity which represents overall myocardial oxidative flux through the TCA cycle (2). The rate constant $K_m$ (min$^{-1}$) will be measured for each myocardial regions of interest (ROI) by fitting a mono-exponential function to the myocardial clearance of $^{11}$C activity. To prevent inclusion of data points outside the linear portion of the $^{11}$C-acetate curve, the first and last data points of the linear portion will be visually chosen by the operator before fitting the data. For a given study, the mean and SD for $K_m$ will be calculated by averaging the $K_m$ values obtained from the three mid-ventricular anterior-lateral ROIs. This value Km will be used in conjunction with echocardiographic measurements of forward LV work.

Oxygen Uptake:

Peak oxygen uptake will be measured at baseline and week 13. Patients will perform a maximal exercise test limited by dyspnea or fatigue on a cycle ergometer. After a rest period, the workloads will increase in a step fashion by 25 watts every 3 minutes. Breath by breath gas exchange and heart rate will be measured throughout exercise. During each 3 minute workload, Borg RPE and blood pressure will be obtained. At peak exercise, heart rate, blood pressure, and Borg RPE will be recorded. Gas exchange endpoints include peak VO$_2$, Ve/VCO$_2$ slope, RER, exercise time, and VO$_2$ and time at ventilatory threshold.

Left Ventricular Ejection Fraction

The exploratory CMR sub-study will include additional measures of LV volumes, RV volumes, biventricular EF and LV mass. The sub-study is not formally powered and recruitment will be based on feasibility. However, the precision of CMR is substantially higher than that of echocardiography: Bellenger, et al. (2000) have estimated as much as an 80% reduction in sample size for measurement of equivalent change in ejection fraction relative to echocardiography.

Left Ventricular Ejection Fraction (Echocardiography)

Echocardiography will be performed at baseline and week 13 using pulse-wave, continuous-wave, tissue Doppler. Endpoints will be comprised of measures of Left ventricular structure and function: Left ventricular end-diastolic and end-systolic volumes (2D), left ventricular ejection fraction (2D), cardiac output, cardiac index and TDI-derived Em (diastolic function).

Left Ventricular Ejection Fraction (CMRI)

Non-contrast CMR will be performed following a period of rest after exercise testing at baseline and after the 3 month treatment phase. A 3T MRI examination will be performed including sequences as recommended by Kramer, et al. (2008) for evaluation of LV structure and function such that the total examination time will not exceed approximately 90 minute. Measurements will be made using quantitative volume analytical methods and reported consistent with recommendations of Cerqueira, et al. (2002).

Six Minute Walk Test (6MWT)

The six minute walk test will be performed at baseline and the end of the study (week 13). All patients will be given standardized instructions and the distance walked will be measured.

Combination of Endpoints

There are multiple scenarios in which a single primary endpoint or combination of endpoints can lead to proof of pharmacodynamic mechanism. For example an observed efficacy in myocardial efficiency coupled with an increase in LVEF or 6MWT is one such scenario.

Example 4

GLP-1 and Cardiovascular Protection

Introduction: Earlier studies have shown that Glucagon-like peptide-1 (GLP-1) elicits cardiovascular benefits independent of its role on peripheral glycemic control. However, the precise mechanism(s) for cardioprotection remains unresolved. This example shows that GLP-1 plays a direct cardioprotective role in rat by enhancing myocardial glucose utilization and promoting an energetically-favorable metabolic substrate switch.

Methods: Sprague Dawley (SD) rats were randomized and administered vehicle or 4.8 pmol/kg/min GLP-1 during 30 min of cardiac ischemia followed by 24 hr of reperfusion (cardiac I/R injury), or 300 pmol/kg/min GLP-1 for up to 3.5 hours (substrate switching). Relative carbohydrate and fatty acid oxidation was measured in normal or I/R injured hearts after 1-$^{13}$C glucose clamp and NMR based isotopomer analysis. $O_2$ consumption was measured in adult rat ventricular myocytes (ARVMs). Glucose utilization and lactate production were assessed using [$^3$H]-2-deoxyglucose or Langendorff perfusion, respectively, in normal hearts.

Results: GLP-1 reduced myocardial infarct size (↓27% of ischemic area, p<0.05, N=6) and increased contractility (↑20% of +dP/dt, p<0.05, N=6) in I/R injured hearts. GLP-1 also induced metabolic substrate switching by increasing the ratio of carbohydrate vs fat oxidation (↑14%, p<0.01, N=6) in the LV non-ischemic border zone. No substrate switching occurred in the LV ischemic zone, despite an increase in cAMP (↑106%, p<0.05, N=5) and lactate (↑121%, p<0.01, N=6). GLP-1 also increased in vivo glucose uptake (↑64%, p<0.05, N=8) in normal hearts, without affecting glycogen levels, and increased glucose uptake and lactate production by 1.9-fold and 2.6-fold, respectively, in Langendorff perfused hearts. Decreased oxygen consumption was observed in GLP-1 treated ARVMs (↓23%, p<0.05, N=4), consistent with a switch from fat to carbohydrate oxidation.

Conclusion: These results show that the cardioprotection observed may be derived via a direct role of GLP-1 on the myocardium. While anaerobic glycolysis may contribute to ischemic cardioprotection, a shift to more energetically favorable carbohydrate oxidation in healthy, non-ischemic myocardium may play a beneficial role in maintaining cardiac contractility.

Any patent application to which this application claims priority is also incorporated by reference herein in its entirety in the manner described above for certain publications and references.

The invention claimed is:

1. A method of providing cardiovascular protection to a human comprising administering to said human a pharmaceutical composition comprising albiglutide.

2. The method of claim 1 wherein the pharmaceutical composition comprises about 3.75 mg, 15 mg or 30 mg of albiglutide.

3. The method of claim 1, wherein the pharmaceutical composition comprises about 4 mg or less of albiglutide.

4. The method of claim 3 wherein the pharmaceutical composition comprises albiglutide in an amount selected from: 1 mg, 1.5 mg, 1.88 mg, 2.0 mg, 2.5 mg, 3.0 mg, 3.25 mg, 3.5 mg, 3.75 mg and 4 mg.

* * * * *

SEQUENCE LISTING

```
<160> NUMBER OF SEQ ID NOS: 2

<210> SEQ ID NO 1
<211> LENGTH: 645
<212> TYPE: PRT
<213> ORGANISM: Homo Sapiens

<400> SEQUENCE: 1

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg His Gly
             20                  25                  30

Glu Gly Thr Phe Thr Ser Asp Val Ser Ser Tyr Leu Glu Gly Gln Ala
         35                  40                  45

Ala Lys Glu Phe Ile Ala Trp Leu Val Lys Gly Arg Asp Ala His Lys
     50                  55                  60

Ser Glu Val Ala His Arg Phe Lys Asp Leu Gly Glu Glu Asn Phe Lys
 65                  70                  75                  80

Ala Leu Val Leu Ile Ala Phe Ala Gln Tyr Leu Gln Gln Cys Pro Phe
```

```
                 85                  90                  95
Glu Asp His Val Lys Leu Val Asn Glu Val Thr Glu Phe Ala Lys Thr
                100                 105                 110
Cys Val Ala Asp Glu Ser Ala Glu Asn Cys Asp Lys Ser Leu His Thr
                115                 120                 125
Leu Phe Gly Asp Lys Leu Cys Thr Val Ala Thr Leu Arg Glu Thr Tyr
                130                 135                 140
Gly Glu Met Ala Asp Cys Cys Ala Lys Gln Pro Glu Arg Asn Glu
145                 150                 155                 160
Cys Phe Leu Gln His Lys Asp Asp Asn Pro Asn Leu Pro Arg Leu Val
                165                 170                 175
Arg Pro Glu Val Asp Val Met Cys Thr Ala Phe His Asp Asn Glu Glu
                180                 185                 190
Thr Phe Leu Lys Lys Tyr Leu Tyr Glu Ile Ala Arg Arg His Pro Tyr
                195                 200                 205
Phe Tyr Ala Pro Glu Leu Leu Phe Phe Ala Lys Arg Tyr Lys Ala Ala
                210                 215                 220
Phe Thr Glu Cys Cys Gln Ala Ala Asp Lys Ala Ala Cys Leu Leu Pro
225                 230                 235                 240
Lys Leu Asp Glu Leu Arg Asp Glu Gly Lys Ala Ser Ser Ala Lys Gln
                245                 250                 255
Arg Leu Lys Cys Ala Ser Leu Gln Lys Phe Gly Glu Arg Ala Phe Lys
                260                 265                 270
Ala Trp Ala Val Ala Arg Leu Ser Gln Arg Phe Pro Lys Ala Glu Phe
                275                 280                 285
Ala Glu Val Ser Lys Leu Val Thr Asp Leu Thr Lys Val His Thr Glu
                290                 295                 300
Cys Cys His Gly Asp Leu Leu Glu Cys Ala Asp Asp Arg Ala Asp Leu
305                 310                 315                 320
Ala Lys Tyr Ile Cys Glu Asn Gln Asp Ser Ile Ser Ser Lys Leu Lys
                325                 330                 335
Glu Cys Cys Glu Lys Pro Leu Leu Glu Lys Ser His Cys Ile Ala Glu
                340                 345                 350
Val Glu Asn Asp Glu Met Pro Ala Asp Leu Pro Ser Leu Ala Ala Asp
                355                 360                 365
Phe Val Glu Ser Lys Asp Val Cys Lys Asn Tyr Ala Glu Ala Lys Asp
                370                 375                 380
Val Phe Leu Gly Met Phe Leu Tyr Glu Tyr Ala Arg Arg His Pro Asp
385                 390                 395                 400
Tyr Ser Val Val Leu Leu Leu Arg Leu Ala Lys Thr Tyr Glu Thr Thr
                405                 410                 415
Leu Glu Lys Cys Cys Ala Ala Ala Asp Pro His Glu Cys Tyr Ala Lys
                420                 425                 430
Val Phe Asp Glu Phe Lys Pro Leu Val Glu Glu Pro Gln Asn Leu Ile
                435                 440                 445
Lys Gln Asn Cys Glu Leu Phe Glu Gln Leu Gly Glu Tyr Lys Phe Gln
                450                 455                 460
Asn Ala Leu Leu Val Arg Tyr Thr Lys Lys Val Pro Gln Val Ser Thr
465                 470                 475                 480
Pro Thr Leu Val Glu Val Ser Arg Asn Leu Gly Lys Val Gly Ser Lys
                485                 490                 495
Cys Cys Lys His Pro Glu Ala Lys Arg Met Pro Cys Ala Glu Asp Tyr
                500                 505                 510
```

```
Leu Ser Val Val Leu Asn Gln Leu Cys Val Leu His Glu Lys Thr Pro
            515                 520                 525

Val Ser Asp Arg Val Thr Lys Cys Cys Thr Glu Ser Leu Val Asn Arg
    530                 535                 540

Arg Pro Cys Phe Ser Ala Leu Glu Val Asp Glu Thr Tyr Val Pro Lys
545                 550                 555                 560

Glu Phe Asn Ala Glu Thr Phe Thr Phe His Ala Asp Ile Cys Thr Leu
                565                 570                 575

Ser Glu Lys Glu Arg Gln Ile Lys Lys Gln Thr Ala Leu Val Glu Leu
            580                 585                 590

Val Lys His Lys Pro Lys Ala Thr Lys Glu Gln Leu Lys Ala Val Met
    595                 600                 605

Asp Asp Phe Ala Ala Phe Val Glu Lys Cys Cys Lys Ala Asp Asp Lys
    610                 615                 620

Glu Thr Cys Phe Ala Glu Glu Gly Lys Lys Leu Val Ala Ala Ser Gln
625                 630                 635                 640

Ala Ala Leu Gly Leu
            645

<210> SEQ ID NO 2
<211> LENGTH: 31
<212> TYPE: PRT
<213> ORGANISM: Homo Sapiens
<220> FEATURE:
<221> NAME/KEY: VARIANT
<222> LOCATION: 31
<223> OTHER INFORMATION: Xaa = Any Amino Acid or -NH2

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30
```